(12) United States Patent
Nagasaki et al.

(10) Patent No.: US 9,862,992 B2
(45) Date of Patent: *Jan. 9, 2018

(54) SURFACE OF SUBSTRATE ONTO WHICH NON-SPECIFIC ADSORPTION IS RESTRAINED

(71) Applicant: JSR Corporation, Tokyo (JP)

(72) Inventors: Yukio Nagasaki, Ibaraki (JP); Tadahito Takahashi, Kanagawa (JP); Kazunori Kataoka, Tokyo (JP); Fumiko Aboshi, Chiba (JP); Miki Kato, Chiba (JP); Tomoko Jomura, Chiba (JP); Hiroshi Kobayashi, Chiba (JP); Yoshinori Katsuyama, Nagareyama (JP); Masami Nakamae, Saitama (JP)

(73) Assignee: JSR CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/459,888

(22) Filed: Aug. 14, 2014

(65) Prior Publication Data

US 2014/0378346 A1 Dec. 25, 2014

Related U.S. Application Data

(62) Division of application No. 10/566,159, filed as application No. PCT/JP2004/011123 on Jul. 28, 2004, now Pat. No. 8,841,138.

(30) Foreign Application Priority Data

Jul. 28, 2003 (JP) ................................ 2003-307964
Dec. 29, 2003 (JP) ................................ 2003-436974

(51) Int. Cl.
*G01N 33/543* (2006.01)
*C12Q 1/68* (2006.01)
*G01N 27/327* (2006.01)

(52) U.S. Cl.
CPC ......... *C12Q 1/6837* (2013.01); *C12Q 1/6834* (2013.01); *G01N 27/327* (2013.01); *G01N 27/3271* (2013.01); *G01N 33/543* (2013.01); *G01N 33/54366* (2013.01); *G01N 33/54393* (2013.01)

(58) Field of Classification Search
CPC ........... G01N 33/543; G01N 33/54366; G01N 33/54393; G01N 27/3271; G01N 27/327; C12Q 1/6837; C12Q 1/6834
See application file for complete search history.

(56) References Cited

U.S. PATENT DOCUMENTS 5,250,613 A 10/1993 Bergstrom et al.
5,919,712 A 7/1999 Herron et al.
6,297,062 B1 10/2001 Gombinski
7,214,500 B2 * 5/2007 Kataoka ............... C08G 65/329
424/78.31
8,841,138 B2 * 9/2014 Nagasaki ......... G01N 33/54366
435/287.2
2003/0040129 A1 2/2003 Shah

FOREIGN PATENT DOCUMENTS

JP 11-211727 8/1999
JP 11-287802 10/1999
WO 01/86301 11/2001
WO 02/056020 7/2002

OTHER PUBLICATIONS

Chapman et al. Preparation of mixed self-assembled monolayer (SAMs) that resist adsorption of proteins using the reaction of amines with a SAM that presents interchin carboxylic anhydride groups. Langmuir 2000, vol. 16, pp. 6927-6936.*
International Search Report dated Sep. 21, 2004, in International (PCT) Application No. PCT/JP2004/011123.
Supplementary European Search Report dated Sep. 28, 2006, in European Application No. 04771169.2.
Qi et al., "Synthesis and characterization of CdS nanoparticles stabilized by double-hydrophilic block copolymers", Nano letters, 2001, vol. 1, No. 2, pp. 61-65.
Kunath et al., "The structure of PEG-modified poly (ethylene imines) influences biodistribution and pharmacokinetis of their complexes with NF-kB decoy in mice", Pharmaceutical Research, 2002, vol. 19, No. 6, pp. 810-817.
Thunemann, "Poly(ethylene oxide)-b-poly(ethylene imine) dodecanoate complexes: Lamellar-within-lamellar morphologies and nanoparticles", Macromolecules, 2001, vol. 34, pp. 6978-6984.
Helmut Colfen, "Double-hydrophilic block copolymer: synthesis and application as novel surfactants and crystal growth modifiers", Macromol. Rapid Commun., 2001, vol. 22, pp. 219-252.
Otsuka et al. "PEGylated nanoparticles for biological and pharmaceutical applications", Advanced Drug Delivery Reviews, 2003, vol. 55, pp. 403-419.
Scott et al., "Synthesis of reagents for one step incorporation of hydrazide functionality onto the lysine residues of proteins, and their use as linkers for carbonyl containing molecules", Bioorganic and Medicinal Chemistry Letters, 1996, vol. 6, No. 13, pp. 1491-1496.
"Modifying aldehydes and ketones with hydrazine and amine derivatives", Handbook of Fluorescent Probes and Research Products, Molecular Probes, 2001.
Hongbo B. Lu et al., "Attachment of Functionalized Poly(ethylene glycol) Films to Gold Surfaces", Langmuir, ACS, Washington, DC, US, vol. 16, Jan. 14, 2000, pp. 1711-1718.

(Continued)

*Primary Examiner* — Shafiqul Haq
(74) *Attorney, Agent, or Firm* — Wenderoth, Lind & Ponack, L.L.P.

(57) ABSTRACT

A substrate surface on which either a substance to detect analyte or an analyte per se is immobilized, which surface is formed by a treatment of substrate surface with a liquid which contains uncrosslinked polymer based on polyethylene glycol chain segment, said treatment conducted either simultaneously with the immobilization of said substance or analyte or after said substance or analyte has been immobilized on said surface. The non-specific adsorption of impurity protein or the like which is co-existent in sample for assay is significantly restrained.

7 Claims, 15 Drawing Sheets

(56) References Cited

OTHER PUBLICATIONS

Maria Teresa Peracchia et al., "Pegylated Nanoparticles from a Novel Methoxypolyethylene Glycol Cyanoacrylate-Hexadecyl Cyanoacrylate Amphiphilic Copolymer", Apr. 1998, Pharmaceutical Research (New York), vol. 15, NR. 4, pp. 550-556.

Kevin L. Prime et al., "Self-Assembled Organic Monolayers: Model Systems for Studying Adsorption of Proteins at Surfaces", Science (Washington D.C.), vol. 252, No. 5009, 1991, pp. 1164-1167.

Takehiko Ishii et al., Preparation of Functionally PEGylated Gold Nanoparticles with Narrow Distribution through Autoreduction of Auric Cation by α-Biotinyl-PEG-block-[poly(2-(N, N-dimethylamino)ethyl methacrylate)], Feb. 3, 2004, Langmuir: The ACS Journal of Surfaces and Colloids, vol. 20, NR3, Feb. 3, 2004, pp. 561-564.

Yoshitsugu Akiyama et al., "Selective Synthesis of Heterobifunctional Poly(ethylene glycol) Derivatives Containing Both Mercapto and Acetal Terminals", Nov. 2000, Bioconjugate Chemistry, vol. 11, NR 6, pp. 947-950.

Michihiro Iijima et al., "Core-Polymerized Reactive Micelles from Heterotelechelic Amphiphilic Block Copolymers", Macromolecules, vol. 32, Jan. 27, 1999, pp. 1140-1146.

\* cited by examiner

Gelatin                Methoxy-PEG-PAMA

MethoxyPEG-PLA 5000    MethoxyPEG-PLA500

SURFACE OF SUBSTRATE ONTO WHICH NON-SPECIFIC ADSORPTION IS RESTRAINED

TECHNICAL FIELD

This invention relates to the surface of substrate, in particular biosensor chip etc., specifically to the surface of substrate which has been treated with uncrosslinked polymer based on polyethylene glycol chain segment, and also to a biosensor which has said surface.

BACKGROUND ART

Immunodiagnosis, biosensor and the like for detecting a certain substance from among biomolecules such as protein or lipid have widely been applied as a means for the early detection or diagnosis of diseases. However, the non-specific adsorption of co-existent biomolecules onto the surface of biosensor which occurs simultaneously with a specific reaction interferes as background noise to prevent the achievement of high sensitivity. In the case of diagnostic particles, furthermore, not only the problem of background caused by non-specific adsorption but also dispersion stabilization in biological fluid or diluted liquid thereof has been a great issue. Inventors of this invention previously found that substrate which has, on its surface, a brush-like structure of water-soluble polymer such as polyethylene glycol not only retrains non-specific adsorption onto sensor surface but also improves dispersion stabilization of nano-particles, and, thus, have provided materials as a new tool of biodiagnosis. As concrete examples of such inventions, a surface with brush-like structure of poly(ethylene oxide) having an increased density (e.g., WO 03/076933 A1), biosensor surface which carries a poly(ethylene glycol) segment-containing polymer derivative (e.g., Japanese Patent KOKAI Publication No. 2003-149245) and dispersion-stabilized functional metal fine particles and semi-conductor fine particles (e.g., Japanese Patent KOKAI Publication No. 2002-080903) can be mentioned.

In the above-mentioned inventions, biomolecules such as antibody are bonded to the tip of brush structure to serve as a system to sense, with high sensitivity, specific reaction such as antigen recognition. However, brush surface is very liable to prevent the adsorption of protein or the like, and, also for some other reasons, it is sometimes difficult to increase the amount of protein such as antibody supported on the tip of brush, which has been a bar to the achievement of high sensitivity. In another method, after antibody or antigen has been bonded to the surface of a solid phase, a polymer which is originated in glycosylethyl (meth)acrylate is adhered to redundant protein-binding sites on the solid phase surface, with a view to preventing the non-specific adsorption of impurity protein or the like which may be contained in sample for assay (Japanese Patent KOKAI Publication No. Hei 10-123135). There has also been proposed another method wherein the surface of a solid phase which is used for immune reaction is protected with a polymer originated in (meth)acrylate which has polyethylene glycol chain in place of the above-mentioned glycosylethyl (Japanese Patent KOKAI Publication No. Hei 11-287802).

These polymers, however, may be sometimes insufficient in bondability or immobilizability onto solid phase surface to which the non-specific adsorption of protein or the like needs to be restrained. Otherwise, when immobilizability is enhanced, it may adversely affect the specific bondability of antibody to antigen in immune reaction. In another proposed method, the affinity of a bio-specific bonding pair, e.g., the affinity between streptoavidin and biotin, is utilized. In detail, a biotinated antibody is bonded to a solid phase which has previously supported streptoavidin, and said solid phase is thereby coated with biotinated polyethylene glycol (Japanese Patent KOKAI Publication No. Hei 11-211727). When this method is to be employed, however, one of companion pieces to bio-specific bonding pair needs to be previously immobilized on solid phase surface.

DISCLOSURE OF INVENTION

Inventors of this invention made researches for the purpose of providing a surface more stable than those of the above-mentioned conventional methods, which is capable of inhibiting non-specific adsorption, and which is easily prepared. As a result, they have found unexpectedly that, on the surface of solid phase (e.g., surface originated in gold, polystyrene or polyvinylidene fluoride) practically used for immunoassay on which antibody, antigen or the like is immobilized, PEG chain brush can be immobilized with no special bonding means, and with no adverse effects produced on the specific bondability of antibody or antigen. Furthermore, in view of the fact that the recognition ability of antibody or the like works depending on the length of PEG chain, the inventors paid consideration, in designing, to the optimization of said length of chain, and, thus, have found a method to conduct specific molecular recognition with high sensitivity.

Thus, this invention provides a substrate surface on which either a substance to detect analyte or an analyte per se is immobilized, which surface is formed by a treatment of substrate surface with a liquid which contains uncrosslinked polymer based on polyethylene glycol chain segment, said treatment conducted either simultaneously with the immobilization of said substance or analyte or after said substance or analyte has been immobilized on said surface.

As a preferable embodiment, this invention provides a substrate surface wherein the above-mentioned uncrosslinked polymer based on polyethylene glycol chain segment is represented by formula (I) as follows:

$$R^1\text{-}L_1\text{-}(CH_2CH_2O)_n\text{-}L_2\text{-}X \quad (I)$$

wherein $R^1$ denotes hydrogen atom, methyl, formyl which may be protected, amino which may be protected, carboxy which may be protected, hydroxyl which may be protected or vinylsulfonyl group;

$L_1$ and $L_2$ independently denote valence bond or linker;

X denotes functional group or functional part to form covalent bond or a bond via physical interaction by which to immobilize said polymer molecule onto the surface of fine porous particles; and n denotes an integer of 2 to 20,000.

As another embodiment, this invention provides a method to produce a substrate surface which comprises (A) preparing a substrate surface, and (B) bringing both an aqueous solution of a substance to detect analyte which has been so modified as to be immobilizable on said substrate surface and a liquid which contains uncrosslinked polymer based on polyethylene glycol chain segment into contact with said substrate surface either simultaneously or in succession, under a condition under which both of said substance and uncrosslinked polymer are quite immobilizable on said substrate surface of (A).

As another embodiment, this invention provides a biosensor which is equipped with the above-mentioned substrate surface.

BEST MODE FOR CARRYING OUT THE INVENTION

Figure 1:
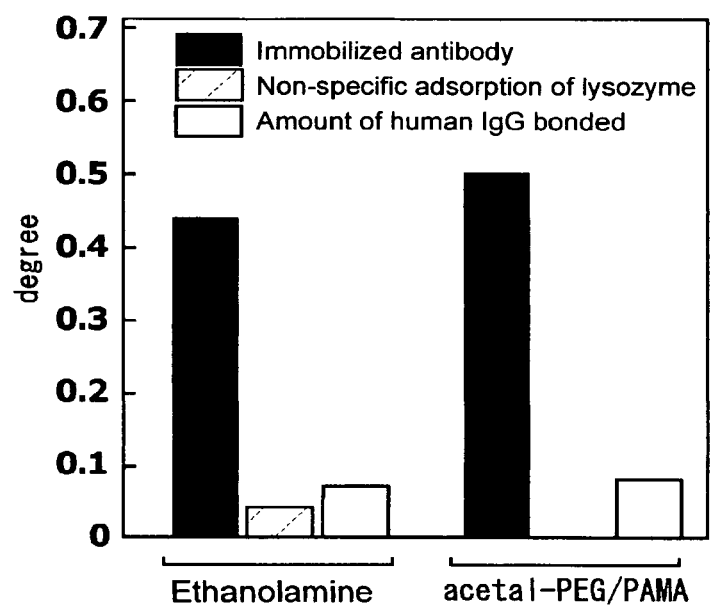
FIG. 1 is a graph which shows both the blocking ability of a surface on which human IgG had been immobilized, and results of sensing of anti-human IgG antibody.

Examples of a substance to detect analyte or an analyte per se as referred to in this invention include bio-specific bonding pair such as antigen or hapten and antibody; oligonucleotide and nucleic acid which hybridizes therewith under stringent condition; enzyme, its substrate sugar and lectin; hormone and its receptor protein; and avidin (including streptoavidin) and biotin (including desthiobiotin, iminobiotin and aminobiotin). Hence, a companion piece to a specific bonding pair means one of counterparts to form the above-mentioned bonding pairs.

Substrate surface on which such a substance (which may include analyte) as mentioned above has been immobilized is a surface, in a solid phase, of bioassay chip or biosensor with which to detect said substance. Any material is usable for such a surface so long as it serves to achieve the objectives of this invention. Preferable examples of substrate surface include electrochemical sensor surface (e.g., made from precious metal, metal oxide, etc.), surface plasmon resonance (SPR) sensor surface (e.g., made from precious metal), quartz sensor surface, microplate surface (e.g., made from polystyrene, polypropylene or polytetrafluoroethylene) for solid phase enzyme-linked immunoassay (ELISA), plastic surface (e.g., made from cellulose derivatives such as nitrocellulose, polyvinylidene fluoride or nylon) for protein blotting or nucleic acid blotting, microarray surface (e.g., made from glass or plastics) for the hybridization of nucleic acid, glass-made surface and silicone-made one (e.g., treated with polydimethyl siloxane), which are usually employed in this field. Preferable examples of the case where substrate and substrate surface become one include gold particle surface, semiconductor particle surface, magnetic particle surface, silica particle surface, fine porous particle surface and surface of particle of latex which contains one of the above-mentioned particles.

One companion piece or the other to a specific bonding pair which has been "so modified as to be immobilizable on said substrate surface" means, when the substrate surface is a gold-deposited membrane, a piece to whose terminal a mercapto group has been introduced in a manner well known in this art.

The substrate surface of this invention is produced by treating a substrate surface with a liquid which contains uncrosslinked polymer based on polyethylene glycol chain segment either simultaneously with the immobilization onto the surface, or after the immobilization onto the surface, of a substance to detect analyte or analyte per se (e.g., one companion piece to specific bonding pair) which has been so modified as to be immobilizable on said substrate surface. Preferably, a substrate surface on which a substance to detect analyte or analyte per se has previously been immobilized is treated with a liquid which contains uncrosslinked polymer based on polyethylene glycol chain segment. In this invention, said substrate surface on which a substance to detect analyte or analyte per se has previously been immobilized includes all surfaces that have been used or suggested for use in this field, such as those which are recited above.

Polymer which is effectively used for the above-explained surface treatment is represented by formula (I). Examples of X in a polymer of formula (I) include, although not restrictive, mercapto group (—SH), silanol group (Si(OH)$_3$), carboxyl group and amino group. In another example, X denotes main chain portion of oligo or polyimino having plural numbers of imino group (—NH—) in the main chain, which has a formula as follows:

wherein $R^2$ denotes hydrogen atom or lower alkyl (e.g., straight or branched chain-alkyl having one to six carbon atoms, such as methyl, ethyl, propyl, isopropyl, n-hexyl, etc., which applies to the following); and m denotes an integer of 1 to 2,000.

In another example, X denotes main chain portion of oligomer or polymer which has, on side chain, mono- or di-lower alkyl-substituted amino group, of a formula as follows:

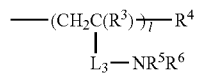

wherein $R^3$, $R^4$, $R^5$ and $R^6$ each independently denote hydrogen atom or lower alkyl group; l denotes an integer of 1 to 2,000; $L_3$ is selected from the group consisting of

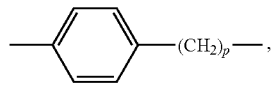

—COO(CH$_2$)$_p$—, —CONH(CH$_2$)$_p$— and —CONR$^7$(CH$_2$)$_p$— wherein p denotes an integer of 1 to 10; and $R^7$ denotes a lower alkyl which may have a hetero atom. Polymers having X as explained above are produced by the method as mentioned in Y. Nagasaki et al., Macromol. Chem. Rapid Commun. 1997, 18, 972, or in Japanese Patent Application No. 2003-49000.

In another example, X denotes main chain portion of oligomer or polymer which has, on side chain, silanol group, of a formula as follows:

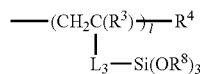

wherein $R^3$, $R^4$ and $L_3$ mean the same as defined above; $R^8$ denotes a lower alkyl, in particular methyl, or a hydrogen atom. Polymers having X as defined above are produced either from trialkoxysilyl as prepared by the method of the above-mentioned Y. Nagasaki et al., or of U.S. Pat. No. 5,929,177, or from the hydrolysis of said trialkoxysilyl where necessary.

In another example, X denotes main chain portion of oligomer or polymer which has, on side chain, carboxyl group, represented by a formula as follows:

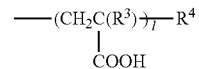

wherein $R^3$, $R^4$ and l mean the same as defined above.

In another example, X denotes main chain portion of oligo or polylactide represented by a formula as follows:

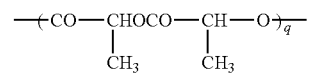

wherein q denotes an integer of 2 to 10,000.

Polymers having X as explained above are mentioned in U.S. Pat. No. 5,925,730 for instance. Other polymers can be produced in accordance with production processes of polymers having various kinds of X, or by modification of the processes.

Incidentally, when X denotes a trimethoxysilyl group, a polymer having said X on a side chain, e.g., a copolymer of monomers of trimethoxysilylpropyl methacrylate and polyethylene glycol (meth)acrylate, having a formula as follows:

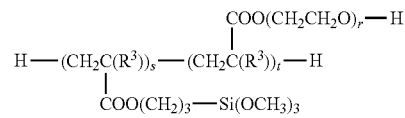

wherein r, s and t independently denote an integer of 2 to 10,000; and $R^3$'s independently denote a hydrogen atom or a methyl group, is included in the polymer of this invention if substrate surface is made from silicone. Such a polymer is useful not only for the above-mentioned treatment of biosensor surface but also for the treatment of capillary electrophoresis column surface and other microcircuit surface. Such a surface is stable against the flow of sample solution, and can furthermore inhibit the adsorption of protein etc. in biosample or the like, thereby preventing clogging.

When $L_1$ in formula (I) denotes a linker, typical examples thereof include, although not restrictive, connecting groups as follows: —(CH$_2$)$_p$—O—, —(CH$_2$)$_q$—COO—,

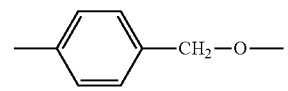

or —(CH$_2$)$_r$—S— wherein p, q and r independently denote an integer of 0 to 8. These linkers are structurally incorporated, in the direction as mentioned, into the portion of $L_1$ in the above-mentioned formula (I).

When $L_2$ denotes a linker, typical examples thereof include, although not restrictive, connecting groups as follows: —(CH$_2$)$_k$—, —CO(CH$_2$)$_l$—,

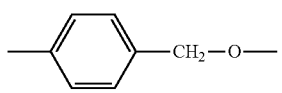

wherein k and l each denote an integer of 1 to 6. These linkers are structurally incorporated, in the direction as mentioned, into the portion of $L_2$ in the above-mentioned formula (I).

Formyl which may be protected in the above-mentioned definition of $R^1$ has a formula as follows:

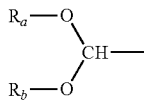

wherein $R_a$ and $R_b$, taken separately, denote lower alkyl, and, taken together, denote methyl-substituted ethylene; or $R_a$—O and $R_b$—O, taken together, denote O= (in which case, formyl OCH— per se is shown). Amino which may be protected, carboxyl which may be protected and hydroxy which may be protected mean groups which are either protected by protective groups known in the field of peptide synthesis or the like, or unprotected. Moreover, protected amino group includes maleimide, and protective group for hydroxyl includes p-toluenesulfonyl group.

The substrate surface of the present invention is prepared in a process which comprises preparing a substrate surface, and bringing both an aqueous solution (including aqueous solution buffered with PBS or the like) of the above-mentioned substance to detect analyte or analyte per se modified and the above-mentioned polymer-containing liquid (water-miscible organic solvent such as methanol, ethanol, tetrahydrofuran, dimethylformamide and dimethylsulfoxide, and aqueous solution which may be buffered with PBS or the like) simultaneously into contact with said substrate surface, under a sufficient condition under which both of said substance and polymer are quite immobilizable onto said substrate surface. As said sufficient condition, there may be mentioned incubation for a time ranging from several to scores of hours at a temperature ranging from 5° C. to a temperature at which the above-mentioned substance is not denatured, e.g., 55° C., although this condition may vary depending on the properties of polymer and substrate surface used. A substrate surface which has the above-mentioned substance previously immobilized thereon is also treated with polymer under almost the same condition as the above. Thus, the substrate surface of the present invention is provided. The above-mentioned polymer is usually used at a proportion of $10^{-6}$ to $10^3$ mg/cm$^2$, preferably $10^{-4}$ to $10^2$ mg/cm$^2$, more desirably $10^{-3}$ to 10 mg/cm$^2$, on the basis of area of substrate surface.

In the following, this invention is explained in more detail with working examples.

Referential Example 1: Production of Acetal-PEG-OH

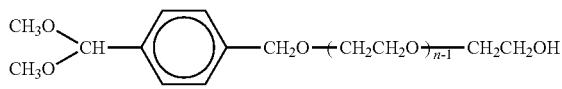

In an egg-shaped flask in an atmosphere of argon at room temperature, 1.0 mmol of 4-hydroxymethyl benzaldehydedimethyl acetal (1.822 mol/l—THF solution, 0.55 ml) as an initiator was added to 25 ml of tetrahydrofuran (THF) as a solvent with a microsyringe, and then, 1.0 mmol of K-naphthalene (0.328 mol/l—THF solution, 3.05 ml) was added, and, thus, metallization was conducted for 10 minutes. Then, 140 mmol of ethyleneoxide (6.9 ml) was added, and the resultant mixture was stirred for two days under water-cooling, and, thus, anion ring-opening polymerization was conducted. Several drops of pure water were subsequently added to stop the reaction, and, then, purification was conducted by diethyl ether precipitation (2 l), chloroform extraction (three times against saturated saline water), drying under reduced pressure and benzene freeze drying. The yield of thus obtained product was 4.5 g (90%).

According to measurement by gel permeation chromatography, the obtained polymer was monomadal, and had a number average molecular weight of 6,067 which almost agreed with theoretical molecular weight of 6,000.

Also measurement by MALDI-TOF-MS (matrix-assisted laser desorption ionization time of flight mass spectrometer) taught that the obtained polymer was monomadal, and had a number average molecular weight of 6,050. Moreover as a result of comparison between measured value and calculated value of the peaks, it was confirmed that this polymer was heterotelechelic polyethyleneoxide which had ethyleneoxide skeleton in its main chain, had acetal group at α-terminal and had hydroxyl group at ω-terminal.

Also from $^1$H-NMR (proton nuclear magnetic resonance) spectrum of the obtained polymer in DMSO, it was confirmed that this polymer was heterotelechelic polyethyleneoxide which had ethyleneoxide skeleton in its main chain, and had acetal group at α-terminal and hydroxyl group at ω-terminal.

Referential Example 2: Production of Benzaldehyde-PEG-OH

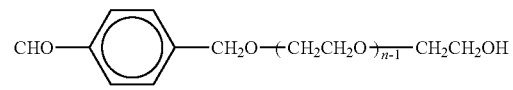

In an egg-shaped flask, 1.0 g of acetal-PEG-OH obtained in the above was dissolved in 20 ml of 90% aqueous solution of acetic acid, and the resulting mixture was stirred for five hours. Subsequently, the mixture was adjusted to pH 8 with use of 10N HCl, and was then dialyzed (molecular weight cut-off: 3500; water was replaced after 1, 2, 4, 6, 8 and 12 hours) against pure water for one day, and was subsequently subjected to drying under reduced pressure and benzene freeze drying, for recovery. The yield of thus recovered product was 0.88 g (88%).

According to measurement of gel permeation chromatography, the obtained polymer was monomadal, and had a number average molecular weight of 6,056 which almost agreed with theoretical molecular weight of 6,054.

Also measurement by MALDI-TOF-MS taught that the obtained polymer was monomadal, and had a number average molecular weight of 6,023. Moreover as a result of comparison between measured value and calculated value of the peaks, it was confirmed that this polymer was benzaldehyde-PEG-OH wherein acetal group at α-terminal had been deprotected.

In $^1$H-NMR (proton nuclear magnetic resonance) spectrum of the obtained polymer in DMSO, spectrum of aldehyde proton was observed near 10 ppm, and, also from this result, it was confirmed that this polymer had become aldehyde (formyl group), with acetal group at α-terminal deprotected.

Referential Example 3: Production of PEHA-Phenyl-PEG-OH

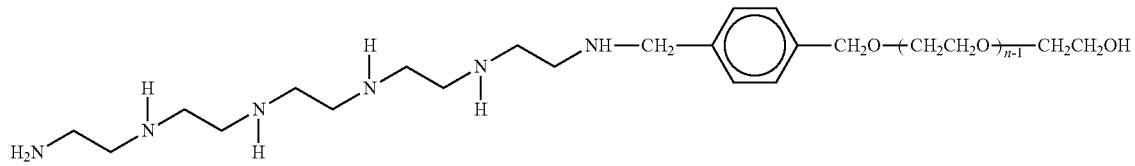

In 5 ml of methanol, 250 mg of benzaldehyde-PEG-OH was dissolved. An egg-shaped flask was fed with PEHA (5 mmol, 1.2 ml) in a molar amount 100 times as much as PEG, and, then, said PEHA was dissolved in 20 ml of methanol. The resultant mixture was adjusted to pH 6 with 5N HCl under ice cooling. To this PEHA methanol solution which was being vigorously stirred, benzaldehyde-PEG-OH methanol solution was slowly added dropwise. The resultant mixture was stirred at room temperature for four hours, and, thus, Schiff base was formed. Then, as a reducing agent, 5 mmol (a molar amount 100 times as much as PEG; about 300 mg) of $NaBH_3CN$ was added to the reaction solution three times in total at an interval of 30 minutes, and the resultant mixture was stirred for 24 hours. Thus obtained reaction solution was dialyzed (molecular weight cut-off: 1000; water was replaced after 3, 6, 18, 24, 30, 42 and 48 hours) against pure water for two days. Subsequently, concentration was adjusted properly by drying under reduced pressure, and, then, the product was recovered by benzene freeze drying. The yield of thus obtained product was 75 mg (30%).

According to measurement of gel permeation chromatography, the obtained polymer was monomadal, and had a number average molecular weight of 5,800 which almost agreed with theoretical molecular weight of 6,270.

In $^1$H-NMR (proton nuclear magnetic resonance) spectrum of the obtained polymer in $D_2O$, spectrum of aldehyde proton which had been observed near 10 ppm in benzaldehyde-PEG-OH had disappeared, and, furthermore, there was newly observed near 3.4 ppm a spectrum which seemed to have been caused by methyl proton between amine and benzene ring. From these results, it was confirmed that PEHA-Phenyl-PEG-OH (or PEHA-Ph-PEG-OH) had been synthesized as desired.

Referential Example 4: Preparation of Magnetic Particles-Supporting Latex

A 200 ml flask was fed with 4 mL of styrene, 45 mL of water and 0.024 g of potassium persulfate, and the resulting mixture was polymerized for 28 hours at 70° C. and 350 rps. It was confirmed by TEM and the measurement of dynamic light scattering that thus obtained latex was monodisperse with an average particle size of 1

A solution of this latex in an amount of 25 mL was mixed with 125 mL of water in a 300 mL flask. After pH was adjusted to 1.7 with hydrochloric acid, there were added $FeCl_3$ (0.405 g) and $FeSO_4$ (0.25 g), and, with vigorous stirring, the resultant mixture was adjusted to pH 9 with ammonia water. Thus obtained ferricolloid latex was easily attracted by magnet, and, thus, it was confirmed that ferrite had been formed on the surface of latex.

Referential Example 5: Preparation of Gold Chip Surface

Gold chip which had been washed with ozone was dipped in acetal-PEG-SH (Mn=5,000) which had been dissolved in 50 mM sodium phosphate buffer (pH 7.4, 1 M NaCl) so that the concentration might be 1 mg/mL, and was then shaken for 30 minutes at room temperature. The chip was washed once with 50 mM sodium phosphate buffer (pH 7.4, 1 M NaCl), and was then dipped in 50 mM sodium hydroxide for 30 seconds, and was again washed three times with 50 mM sodium phosphate buffer (pH 7.4, 1 M NaCl). This operation was repeated twice. Furthermore, the chip was dipped in MeO-PEG-SH (Mn=2,000) which had been dissolved in 50 mM sodium phosphate buffer (pH 7.4, 1 M NaCl) so that the concentration might be 1 mg/mL, and was then shaken for 30 minutes at room temperature. The chip was washed once with 50 mM sodium phosphate buffer (pH 7.4, 1 M NaCl), and was then dipped in 50 mM sodium hydroxide for 30 seconds, and, subsequently, the surface of gold chip was again washed three times with 50 mM sodium phosphate buffer (pH 7.4, 1 M NaCl).

This operation was repeated twice, and, thus, the surface of gold chip was modified with PEG (preparation of mixed brush). Then, PEG-modified gold chip was dipped in 0.1 mol/L hydrochloric acid, and was then shaken mildly for three hours at room temperature, and, thus, acetal group at PEG terminal was converted into aldehyde group. Then, the gold chip was dipped in biocytin-hydrazide (EZ-Link®; PIERCE) which had been dissolved in 100 mM sodium phosphate buffer (pH 5.5, 1 M NaCl) so that the concentration might be 1 mg/mL, and was then shaken for three hours at room temperature, and, thus, biotin was introduced to the surface of gold chip.

Example 1

Preparation of Surface on Gold Surface

Gold substrate (manufactured by Nippon Laser Electronics LAB) which had been washed with ozone was dipped in 1 mM 4,4'-dithiodibutyric acid (solvent: ethanol) for at least 12 hours in a Petri dish at room temperature, and was thereafter washed with ethanol. A mixed solution of 25 mg of EDC (1-ethyl-3-(3-dimethylaminopropyl) carbodiimide) which had been dissolved in 1 mL of distilled water and 15 mg of NHS(N-hydroxysuccinimide) which had been dissolved in 9 ml of dioxane was added to Petri dish. Substrate which had been washed was dipped in the mixed solution, and was then mildly shaken for 30 minutes and was thus activated.

Thus activated substrate was set in a surface plasmon sensor (SPR manufactured by Nippon Laser Electronics LAB), and, then, 1 µM human IgG was immobilized on surface layer under a condition of 25° C., 5·L/min, 60 μL. On thus prepared IgG-immobilized surface, there were twice injected ethanolamine (pH 8.6) and 1 mg/mL acetal-polyethyleneglycol-b-poly(methacrylic acid 2-N,N-dimethylaminoethyl) (hereinafter referred to as Acetal-PEG/PAMA; PEG chain length and PAMA chain length were 5660 and 2780 respectively; hereinafter abbreviated as (5660/2780)) under a condition of 25° C., 5 L/min, 60 μL. Thus obtained surface was measured for non-specific adsorptivity and specific adsorptivity with spr. As is shown by FIG. 1, non-specific adsorptivity of lysozyme on the surface which had been blocked with ethanolamine was $4 \times 10^{-2}$ (°), whereas the surface which had been blocked with acetal-PEG/PAMA (5660/2780) inhibited non-specific adsorption almost completely. It was also confirmed that anti-human IgG antibody which had been brought into contact was efficiently detected.

Referential Example 6: Method to Prepare Biotin-Labeled BSA

To 5 mg of BSA (Cohn Fraction V, WAKO) which had been dissolved in 1 ml of 50 mM carbonic acid buffer (pH 9.6), there was added 21 μl of biotin-$(AC_5)_2$—OSu (DO-JINDO) which had been dissolved in DMSO so that the concentration might be 20 mg/ml, and, thus, the resulting mixture was made to react for two hours at room temperature. The mixture was gel filtrated, and unreacted biotin-$(AC_5)_2$—OSu was thereby removed, and, furthermore, the buffer was replaced with 20 mM sodium phosphate buffer (pH 7.5, 0.15 M NaCl, 1 mM EDTA). The amount of thus obtained biotin-labeled BSA was determined by HABA method. It was confirmed that about five molecules of biotin had been introduced per molecule of BSA.

Example 2: Preparation of Streptoavidin Gold Colloid Particles, and Stabilization with Acetal-PEG-PAMA (4500/3200) (to be Referred to as SAGCPEG/PAMA (4500/3200))

To gold colloid solution (PolyScience; average particle size: 40 nm; concentration: 0.01%), there was added an aqueous solution of streptoavidin (ImmunoPure) in an amount of $10^3$ times as much as the gold colloid solution, and the resultant mixture was incubated at room temperature for one hour, and, thus, streptoavidin was adsorbed on the surface of gold particles. Then, an aqueous solution of acetal-PEG-PAMA (4500/3200) was added so that the molar ratio of gold particles to polymer might be $1:1 \times 10^6$, and the resultant mixture was made to react at 4° C. overnight. Thereafter, an operation of centrifugation [4° C., 4000×g, 30 minutes] to recover precipitated residue was repeated three times, and, thus, superfluous streptoavidin and polymer were removed.

It was confirmed by UV-Vis spectrometry that thus obtained PEG-modified gold colloid particles showed good re-dispersibility after centrifugation purification, and existed stably in 10 mM sodium phosphate buffer (pH 7.4, 0.15 M NaCl).

Figure 2:
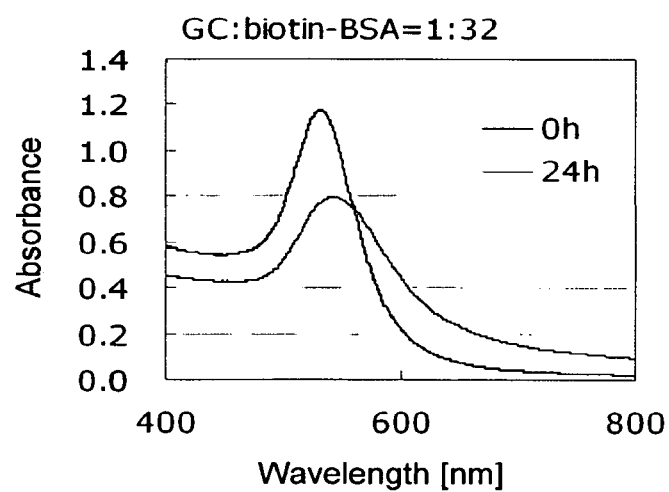
FIG. 2 shows the change of absorbance before and after the addition of biotinated BSA to streptoavidin-immobilized PEGlated gold colloid.

The recognition ability of thus obtained streptoavidin-supporting PEGated gold colloid was examined by molecule recognition test with agglutination test. When biotin-introduced BSA as prepared in Referential Example 6 was added to PEG-modified streptoavidin gold colloid particles, the shift of peak top at absorption spectrum (800 nm-400 nm) was observed, and, thus, interaction between streptoavidin on the surface of gold colloid and biotin was confirmed (FIG. 2).

Example 3: Preparation of Streptoavidin-Supporting Gold Colloid Particles, and Stabilization with Acetal-PEG-SH (Mn=10,000, 5,000) (to be Referred to as SAGCPEG/SH (10,000) and SAGCPEG/SH (5,000))

Streptoavidin-supporting PEGated gold colloid was prepared in just the same manner as in Example 2 except that acetal-PEG-PAMA (4500/3200) was replaced with MeO-PEG-SH (Mn=10,000) and MeO-PEG-SH (Mn=5,000). The dispersion stability of thus obtained streptoavidin-supporting PEGated gold colloid was remarkably high as in Example 2.

Referential Example 7: Preparation of Bovine Serum Albumin (BSA)-Supporting PEGated Gold Colloid, and Stabilization with Acetal-PEG-PAMA (4500/3200) (to be Referred to as BSAGCPEG/PAMA (4500/3200))

Streptoavidin-supporting PEGated gold colloid was prepared in just the same manner as in Example 2 except that streptoavidin was replaced with BSA. The dispersion stability of thus obtained BSA-supporting PEGated gold colloid was remarkably high as in Example 2.

Referential Example 8: Preparation of Bovine Serum Albumin (BSA)-Supporting PEGated Gold Colloid, and Stabilization with Acetal-PEG-SH (Mn=5,000) (to be Referred to as BSAGCPEG/SH (5,000))

Streptoavidin-supporting PEGated gold colloid was prepared in just the same manner as in Example 3 except that streptoavidin was replaced with BSA. The dispersion stability of thus obtained BSA-supporting PEGated gold colloid was remarkably high as in Example 2.

Example 4: Confirmation of Molecule-Recognizing Ability of Streptoavidin- and BSA-Supporting PEGated Gold Colloid Molecule-recognizing ability of thus obtained dispersion-stabilized streptoavidin- and BSA-supporting PEGated gold colloid was confirmed with spr (BIAcore 1000). PEGated gold surface having biotin which had been prepared in Referential Example 5 was made to react with modified gold colloid particles which had been dissolved in 50 mM sodium phosphate buffer (pH 7.4, 0.15 M NaCl) containing 1% BSA at a measurement temperature of 25° C. and a flow rate of 10·L/min, and, thus, the change of angle was measured by surface plasmon resonance method.

Figure 3:
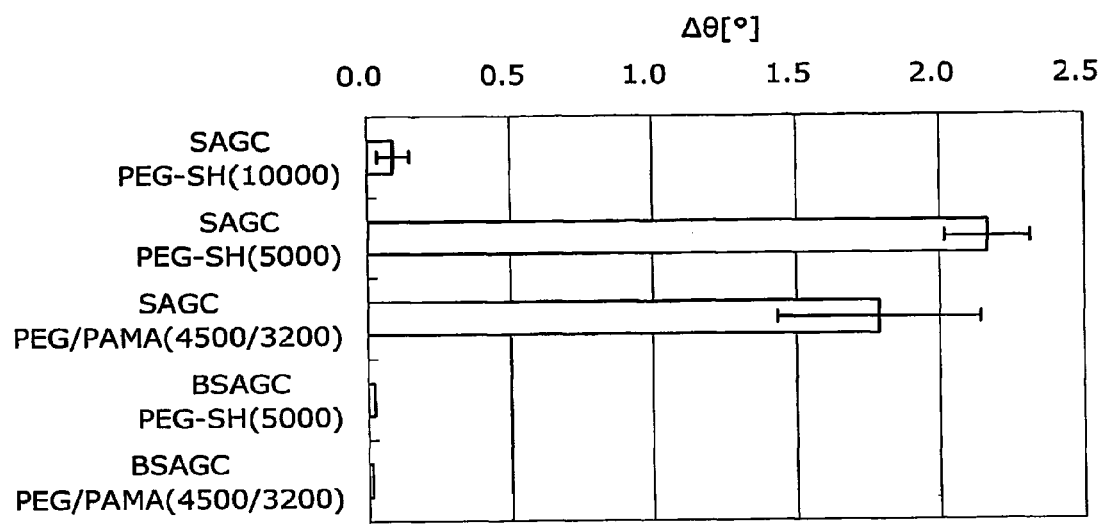
FIG. 3 is a graph which shows the change at sensor gram when streptoavidin-supporting and BSA-supporting PEGlated gold colloid solutions were brought into contact with spr sensor which had biotin-PEG brush surface.

FIG. 3 shows the results of spr. BSA-supporting gold colloid was hardly recognized on biotinated spr surface. Streptoavidin-supporting PEGated gold colloid having a PEG chain of 10,000 also gave small spr signal. Gold colloid which had been treated with PEG 5,000 and PEG-PAMA (4500/3200), however, gave a very strong signal, and, thus, it was confirmed that streptoavidin supported on gold colloid efficiently interacted with biotin on the surface of spr sensor.

Example 5: Preparation of Anti-Biotin Antibody-Supporting Gold Colloid Particles, and Stabilization with Acetal-PEG-PAMA (5660/2780)

Anti-biotin antibody-supporting PEGated gold colloid was prepared in just the same manner as in Example 2 except that streptoavidin and acetal-PEG-PAMA (4500/3200) were replaced with anti-biotin antibody and acetal-PEG-PAMA (5660/2780). It was confirmed that thus obtained anti-biotin antibody-supporting PEGated gold colloid had been dispersion-stabilized.

Example 6: Preparation of Anti-Biotin Antibody-Supporting Gold Colloid Particles, and Stabilization with Acetal-PEG-SH (Mn=10,000, 5,000)

Anti-biotin antibody-supporting PEGated gold colloid was prepared in just the same manner as in Example 3 except that streptoavidin was replaced with anti-biotin antibody. It was confirmed that thus obtained anti-biotin antibody-supporting PEGated gold colloid had been dispersion-stabilized.

Example 7: Confirmation of Molecule Recognition of Anti-Biotin Antibody-Supporting PEGated Gold Colloid Molecule-recognizing ability of thus obtained dispersion-stabilized anti-biotin antibody-supporting PEGated gold colloid was confirmed with spr (BIAcore 1000) in just the same manner as in Example 4.

Figure 4:
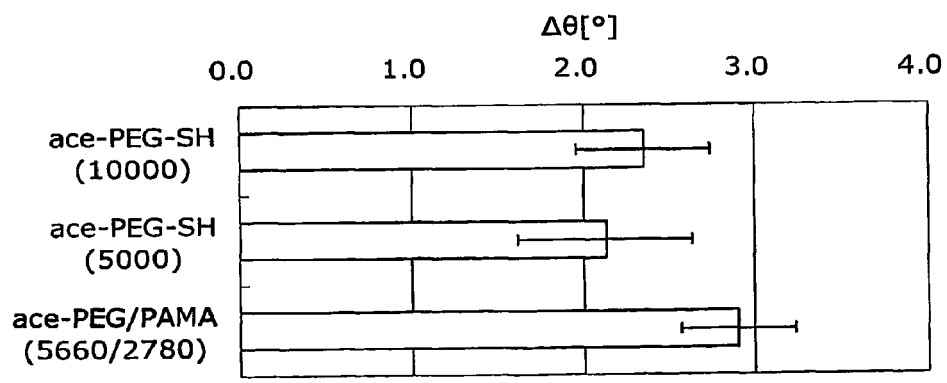
FIG. 4 is a graph which shows the change at sensor gram when antibiotin antibody-supporting PEGlated gold colloid solution was brought into contact with spr sensor which had biotin-PEG brush surface.

FIG. 4 shows the results of spr. Antibody-supporting gold colloid detected a signal with high sensitivity also in the case of ace-PEG-SH (10,000) where streptoavidin-supporting PEGated gold colloid (Mn=10,000) was unable to detect a signal. Thus, there was provided antibody-supporting gold colloid having specific recognition ability.

Example 8: PEG Blocking on the Surface of Magnetic Particles

Ferrite-supporting latex as prepared in Referential Example 4 was surface-treated with acetal-PEG/PAMA. As shown in Table 1, a certain amount of acetal-PEG/PAMA was put in a sample tube, in which 5 ml of 10 mM phosphate buffer (pH=7.18) was added, and, then, the resultant mixture was stirred and dissolved. To the resultant solution, magnetic latex was added, and stirred, and, subsequently, the resultant mixture was subjected to washing operation (phosphate buffer×four times), and, thus, unadsorbed PEG-b-PAMA was removed. After the washing operation was over, dispersion stability was examined, and, then, zeta potential measurement was conducted with a view to confirming surface charge of ferrite particles.

TABLE 1

| Condition of acetal-PEG/PAMA surface treatment | | |
|---|---|---|
| Run | Ferrite latex (mg) | Acetal-PEG/PAMA (mg) |
| 1 | 0.5 | 0 |
| 2 | 0.5 | 0.61 |
| 3 | 0.5 | 5.13 |
| 4 | 0.5 | 24.96 |

Phosphate buffer: 5 mL (pH = 7.1; ionic intensity: 10 mM)

Figure 5:
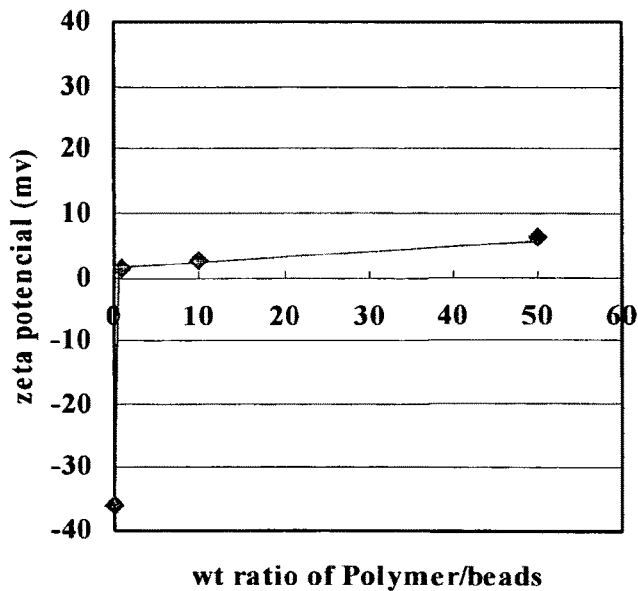
FIG. 5 is a graph which shows the relation between the condition of surface treatment of magnetic latex with acetal-PEG/PAMA and zeta potential.

As is shown by FIG. 5, the zeta potential of untreated latex was −40 mV, a negative value. It was confirmed, on the other hand, that the surface potential of block-coated latex had almost completely been shielded, and that the coating was perfect.

Figure 6:
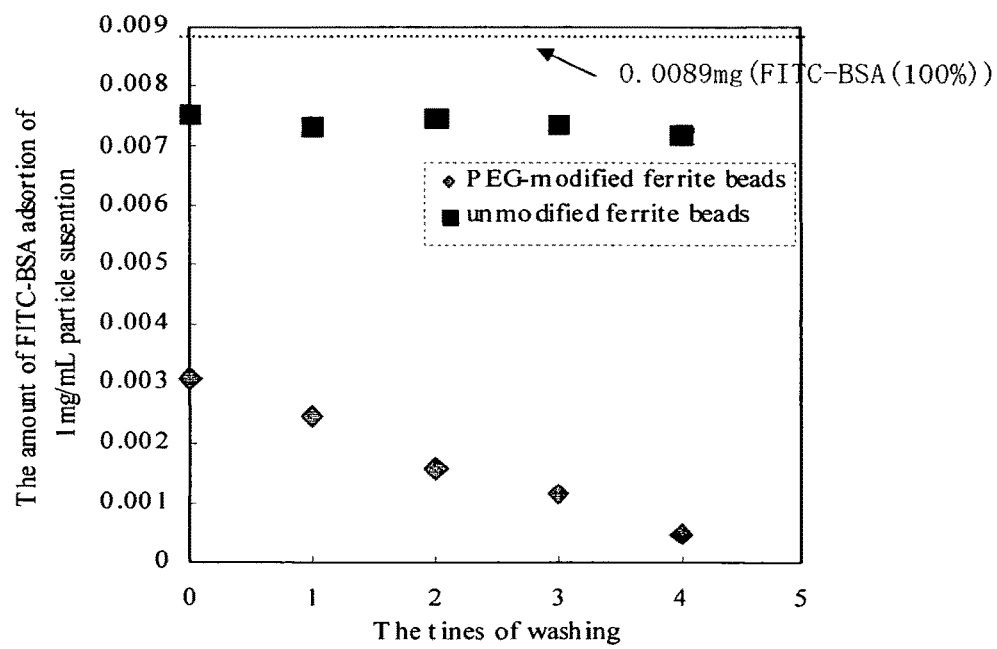
FIG. 6 is a graph which shows the dependency, on the times of washing, of the amount of bovine serum albumin adsorbed on magnetic latex whose surface had, or had not been, treated with acetal-PEG/PAMA.

Thus prepared acetal-PEG/PAMA coated magnetic latex was evaluated with regard to non-specific adsorption of protein. Magnetic latex in an amount of 2.5 mg was treated with 3.2 mg of acetal-PEG/PAMA under the same condition as mentioned above. Apart from that, untreated magnetic latex in an amount of 2.5 mg was prepared. Each of these magnetic latex was mixed with 17.8·g of solution of FITC-BSA which had been dissolved in 2 mL of phosphate buffer (pH=7.1; I=10 mM). After one hour, particles were separated with a magnet, and supernatant was measured with use of a spectrofluorometer for the intensity of fluorescence at emission wave length of 520 nm corresponding to excitation wave length of 490 nm, and, thus, the amount of FITC-BSA was calculated. FIG. 6 shows the amount of FITC-BSA adsorbed on the surface of particles, corresponding to the times of washing. Washing did not peel protein off particles which had not been coated with block polymer, whereas protein was peeled off coated particles almost completely after four times of washing, and, thus, it was confirmed that non-specific adsorption was inhibited.

Example 9: Method of Preparation of Magnetic Particles Having PEG Brush on their Surface (2)

Surface treatment was conducted in the same manner as in Example 8 except that magnetic latex as prepared in Referential Example 4 was replaced with magnetic particles of JSR. Magnetic particles in an amount of 0.5 mg were surface-treated with acetal-PEG/PAMA in the same amount as the magnetic particles, and then in an amount 10 times as much as the magnetic particles. Thus treated particles showed remarkably increased dispersibility, as compared with untreated latex. Untreated particles had a high sedimentation rate, and was therefore unable to be measured for zeta potential. Polymer-treated particles, on the other hand, had a zeta potential of −4 mV and +1 mV, and, thus, it was confirmed that surface had been shielded.

Example 10: Method Wherein Magnetic Particles (Dynabeads) Having Tosyl Group are Made to Support Antibody, and are Thereafter Surface-Blocked with Acetal-PEG/Polyamine Eppendorf tube was fed with 46.9·L of 10 mM tris buffer solution (TBS solution; pH=8.12; 0.15 M NaCl) of dynabeads (the amount of dynabeads: 93.75·g) and 150 μL of Goat-IgG/10 mM tris buffer solution (TBS solution; pH=8.12) (the amount of antibody: 30 μg), and, then, the resultant mixture was allowed to react for 30 minutes at 37° C. After recovered with magnet, particles were washed three times with 10 mM TBS (pH=8.12) with a view to removing unreacted matters.

To magnetic particles which supported antibody in the above-mentioned manner, 150 μL of a blocking agent/TB solution was added, and, then, the resultant mixture was allowed to react for one hour at room temperature. After reaction was over, the particles were washed three times with 10 mM TBS (pH=8.12) with a view to removing unreacted matters. After washing was over, 150 μL of Anti-Goat-IgG/TB solution was added, and, then, the resultant mixture was allowed to react for one hour at room temperature. After reaction was over, the particles were washed three times with 10 mM TBS (pH=8.12) with a view to removing unreacted matters. After washing was over, the particles were dispensed in a white 96-well plate, and, then, 100 μL of 4-MUP (4-methylumbelliferyl phosphate; Sigma) was added as a substrate. The resultant mixture was allowed to react for 30 minutes at room temperature, and, thereafter, 35 μL, of 0.5 M aqueous solution of NaOH was added to stop the reaction. After the reaction was over, particles were separated with magnet, and, then, supernatant was dispensed in a black 96-well plate, and was measured by a microplate reader for the intensity of fluorescence at emission wave length of 460 nm corresponding to excitation wave length of 355 nm. Thus, Goat-IgG which had bonded to the surface of particles was detected. Conditions of this experiment are as shown in Table 2.

To each of 10 μL of 50% NRS (normal rabbit serum)/PBS, 1% BSA/PBS and NHS (normal human serum), there were added 50 μL of 1% BSA/PBS and 50 μL of solution of magnetic particles. After stirred with vortex, the resultant mixture was shaken for one hour, and was thus allowed to react. The particles were separated by magnet, and were then washed twice with TBST (tris buffer which contained 0.15 M NaCl and 0.05% of TWEEN 20). Subsequently, 50 uL of anti-AFP-monoclonal antibody (stock solution on the market (Wako 016-14511) was diluted to the concentration of 1/5000) was added, and the resultant mixture was shaken for one hour, and was thus allowed to react. Then, the particles were separated by magnet, and were washed (in the same manner as above). Thereafter, anti-mouse alkaliphosphatase IgG antibody (stock solution of anti-mouse (goat)-alkali-

TABLE 2

Conditions for experiment of making dynabeads support antibody, and of blocking the dynabeads

| Run | Beads (μg) | Goat IgG (μg) | Glycine (μL) | PEG-b-PAMA (μL) | PEHA-PEG (μL) | BSA (μL) | Anti Goat IgG ALP conjugate (μL) | 4-MUP (μL) | 0.5M NaOH aq (μL) |
|---|---|---|---|---|---|---|---|---|---|
| A-1 | 31.25 | 10 | 50 (1 wt %) | 50 (P/B = 1) | — |  |  |  |  |
| A-2 | 31.25 |  | 50 (10 wt %) | 50 (P/B = 1) | — |  |  |  |  |
| A-3 | 31.25 |  | — | — | 50 (P/B = 1) | — | 50 | 100 | 35 |
| A-4 | 31.25 |  | — | — | 50 (P/B = 10) | — |  |  |  |
| A-5 | 31.25 |  | — | — | — | 50 |  |  |  |
| C-1 | 31.25 | — | 50 (1 wt %) | 50 | — | — |  |  |  |
| C-2 | 31.25 |  | 50 (10 wt %) | 50 | — | — |  |  |  |
| C-3 | 31.25 |  | — | — | 50 | — | 50 | 100 | 35 |
| C-4 | 31.25 |  | — | — | 50 | — |  |  |  |
| C-5 | 31.25 |  | — | — | — | 50 |  |  |  |

Figure 7:
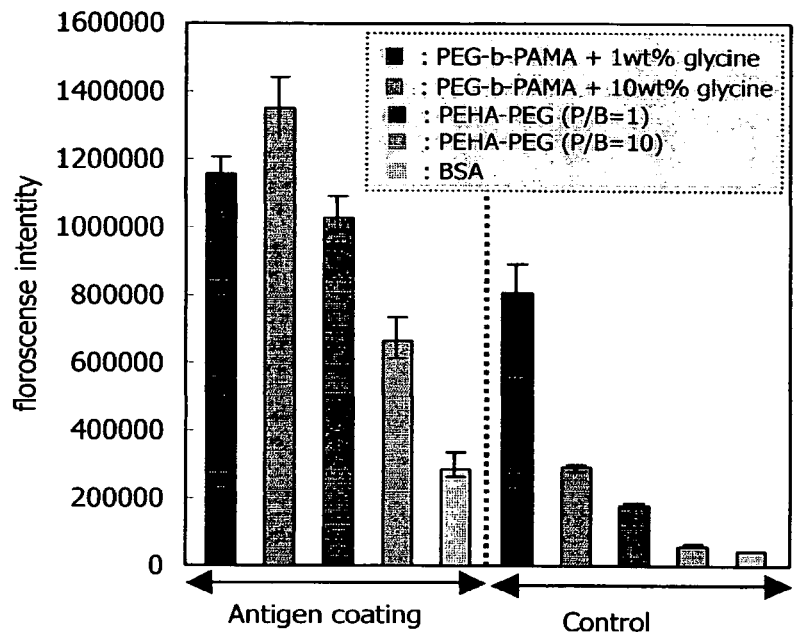
FIG. 7 shows a comparison of the detecting ability of anti-goat IgG when goat IgG antibody-supporting dynabeads were coated with block polymer. Five data on the left side show sensing ability of particles, and five data on the right show non-specific adsorption onto particles which support no antibody on their surface.
Figure 8:
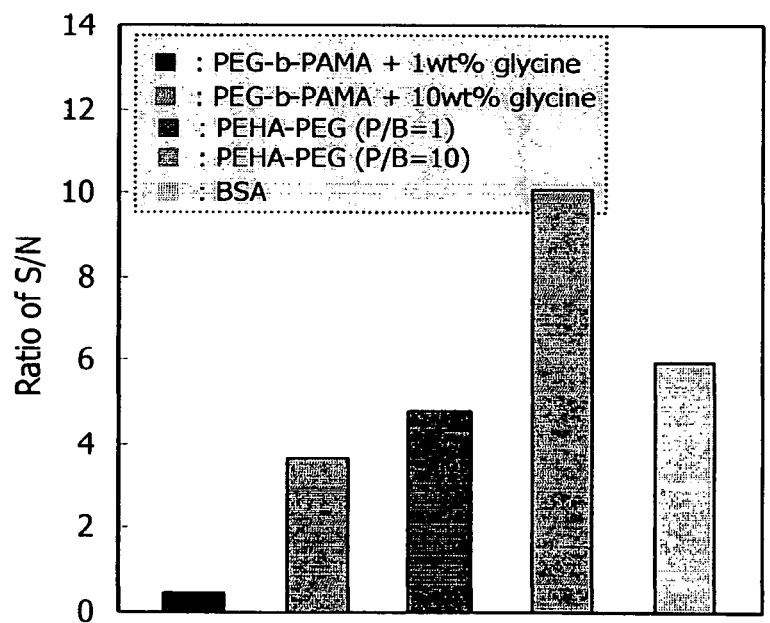
FIG. 8 is a graph which shows S/N as obtained from FIG. 6. PEHA-Ph-PEG-OH exhibits the best blocking performance.

10 mMTB: Trizma-base: 1.0M HCl: distilled water: pH = 8.12
10 mMTBS: Trizma-base: 1.0M HCl: distilled water: pH = 8.15 0.15M NaCl
1 wt % glycine/TB: Glycine in an amount of 0.5 g was dissolved in 50 mL of 10 mMTB.
10 wt % glycine/TB: Glycine in an amount of 5 g was dissolved in 50 mL of 10 mMTB.
BSA/TB: BSA in an amount of 15 mg was dissolved in 2 mL of 10 mMTB (pH = 8.12).
PEG-b-PAMA/TB: PEG-b-PAMA in an amount of 1 mg was dissolved in 5 mL of 10 mMTB (pH = 8.12).
PEHA-Ph-PEG/TB: PEHA-Ph-PEG in an amount of 1 mg was dissolved in mL of 10 mMTB (pH = 8.12).
Anti-Goat IgG ALP conjugate: Stock solution was diluted to the strength of 1/30,000.
4-MUP (Substrate): 4-Methylumbelliferyl phosphate FIG. 7 shows results of evaluation of the ability to detect antigen which had been bonded to dynabeads, and FIG. 8 shows S/N ratio of the systems. In FIG. 7, the intensity of luminescence which was caused by a reaction between enzyme (ALP) and substrate (4-MUP) in control system was in the following order: "PEG-b-PAMA+1 wt % glycine">"PEG-b-PAMA+10 wt % glycine">"PEHA-Ph-PEG (P/B=1)">"PEHA-Ph-PEG (P/B=10)">"BSA". As is seen in FIG. 8, S/N ratio of the systems was in the following order: "PEHA-Ph-PEG (P/B=10)">"BSA">"PEHA-Ph-PEG (P/B=1)">"PEG-b-PAMA+10 wt % glycine">"PEG-b-PAMA+1 wt % glycine". From this result, it is known that the system of PEHA-Ph-PEG (P/B=10) was the best as a blocking agent.

Example 11: Surface Treatment with PEHA-Phenyl-PEG-OH (JSR Magnetic Particles)

PEHA-Phenyl-PEG-OH at the concentration of 0, 0.5, 1.0, 2.0, 3.0 and 4.0 wt % was mixed with a solution of JSR magnetic particles (supporting anti-AFP rabbit antibody, 7 ug/mg beads (0.35 ug/test), carboxylic acid surface particles, magnetic particles: 10 mg/ml) at a proportion of 1:1. After stirred with vortex, the resultant mixture was rotated overnight at 4° C., and, thus, surface treatment was conducted. Then, the mixture was diluted to the concentration of 1/10 with 1% BSA.

phosphatase conjugate (Sigma A3688) was diluted to the concentration of 1/5000; 1% BSA/PBS) was added, and the resultant mixture was shaken for one hour, and was thus allowed to react. After washing, 120 uL of substrate solution of 4MUP (Sigma) was added, and, after stirring, the resultant mixture was left to stand still for 30 minutes at room temperature. Then, 40 μL of 0.5 N NaOH was added to stop reaction. To a plate (Nunc 437111), 100 uL of the resultant solution was moved, and was measured with a plate reader (Ex/Em=$^{355}$/$_{460}$ nm).

Figure 9:
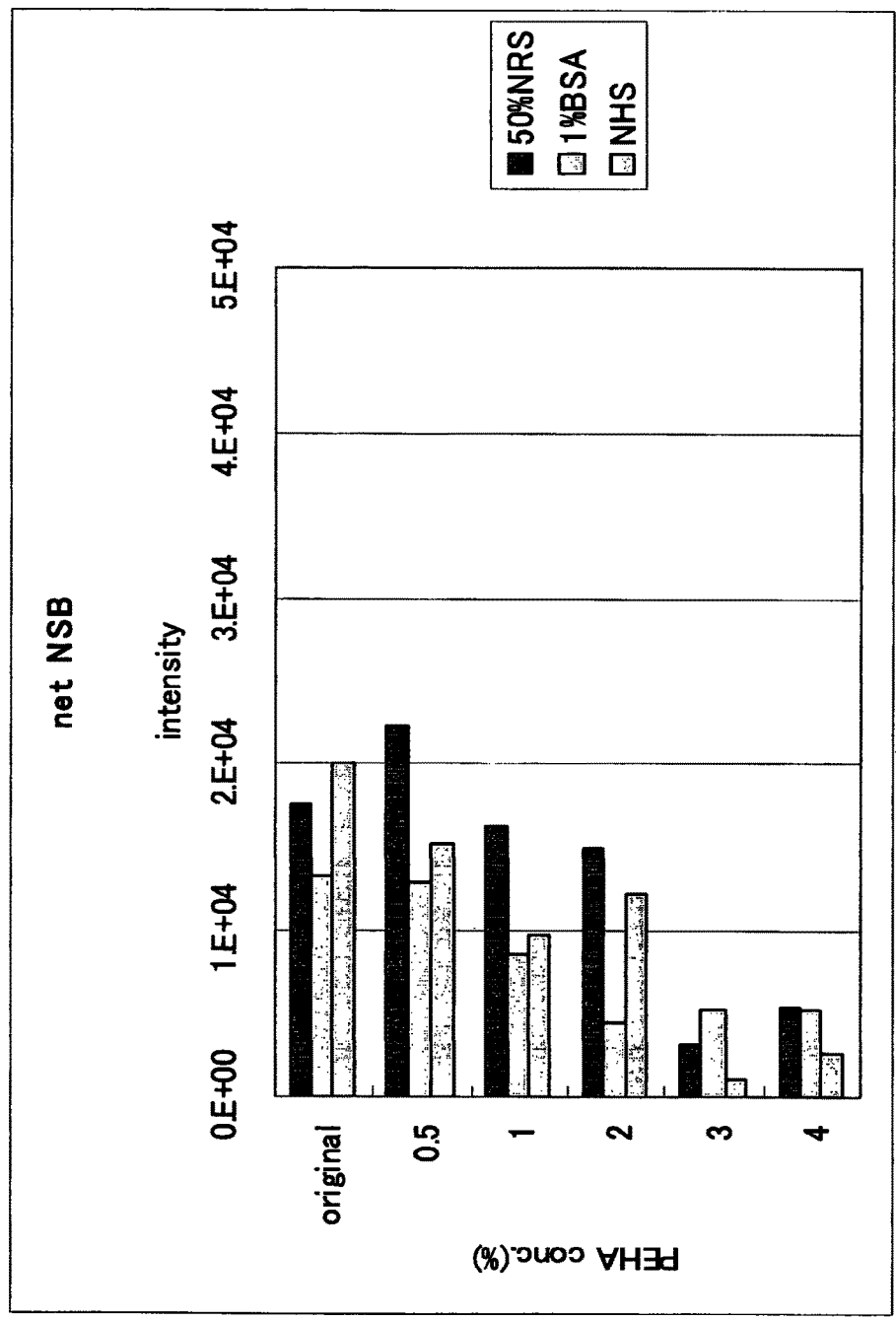
FIG. 9 is a graph which shows the result of surface treatment of JSR antibody-supporting magnetic particles with PEHA-Ph-PEG-OH. It is seen that non-specific adsorption is markedly inhibited.
Figure 10:
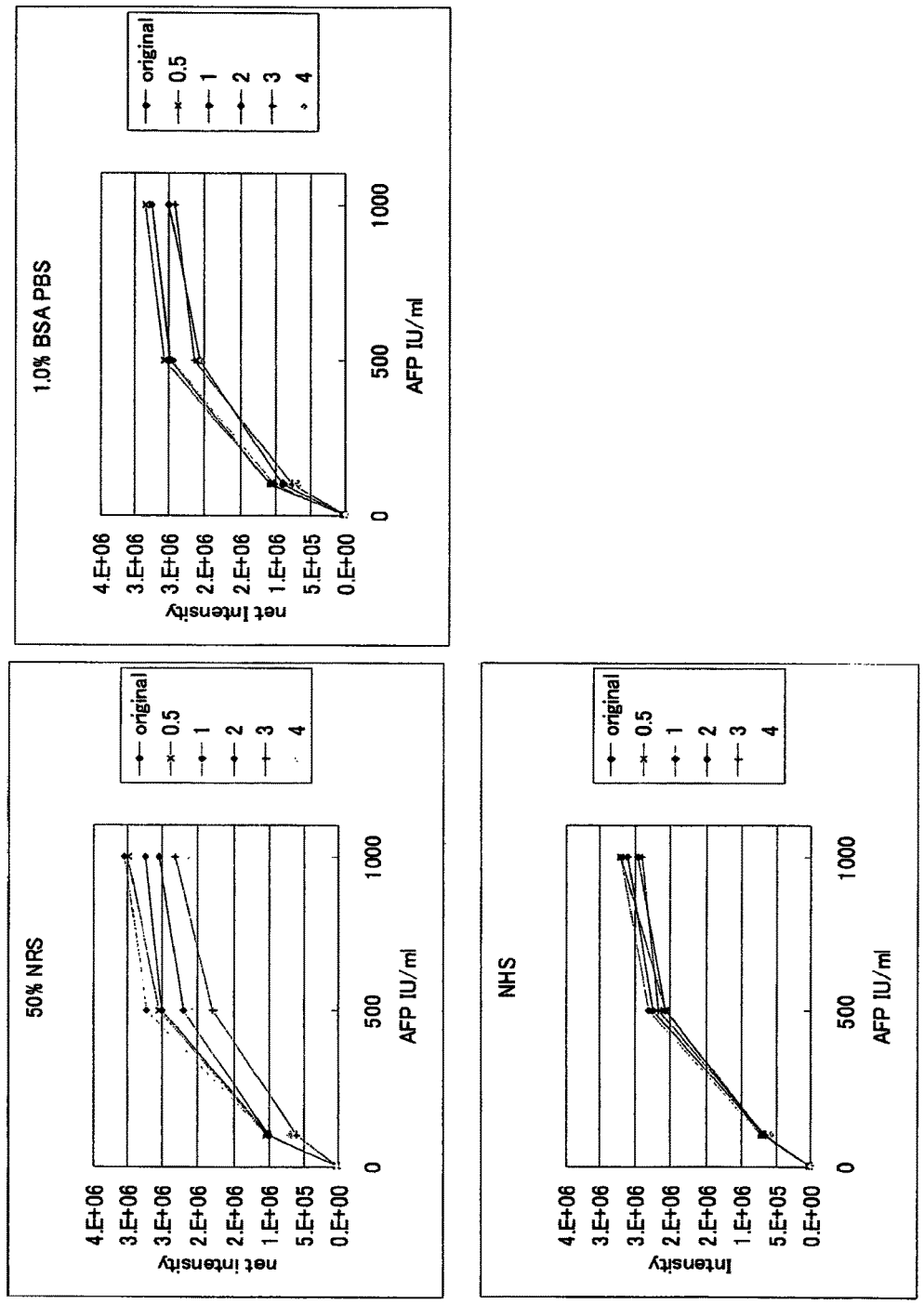
FIG. 10 is a graph which shows the result of surface treatment of JSR antibody-supporting magnetic particles with PEHA-Ph-PEG-OH. It is seen that antigen-detecting ability was high enough.

It was confirmed, as is shown by FIG. 9, that the treatment with PEHA-Phenyl-PEG-OH inhibited non-specific adsorption or non-specific bonding (NSB). Furthermore, high sensitivity detection was achieved, as shown by FIG. 10.

Example 12

Before primary antibody of Example 11 was added, AFP (α-feto protein; Aspen Bio Inc. 105S (Lot 990628V1SS) 500 K IU/mg) was diluted to 5, 100, 500 and 1,000 IU/ml with 50% NRS, 1% BSA PBS and NHS, and was each added to magnetic particles. Then, measurement was conducted in otherwise the same manner as in Example 11. It was confirmed that AFP was detected in spite of the blocking with PEHA-Phenyl-PEG-OH.

Example 13: Blocking of Dynabeads (Surface Tosyl Group) with PEHA-Phenyl-PEG-OH ① A tube was fed with a certain amount of beads solution and antigen solution, and the resultant mixture was made to react for 1.0 hour at room temperature, and, then, the beads were washed with TBS.
② PEHA-Phenyl-PEG-OH was added to ①, and the resultant mixture was made to react for 1.0 hour at room temperature, and, then, the beads were washed with TBS.
③ ② was dispensed to a 96-well plate, and, then, antibody solution was added, and the resultant mixture was made to react for 1.0 hour at room temperature, and, then, the beads were washed with TBS (the same method as in Example 12).
③ Substrate (4-MUP) was added to ③, and the resultant mixture was made to react for 0.5 hour at room temperature, and, then, 0.5 M aqueous solution of NaOH was added to stop the reaction.
④ Beads were immobilized with magnet, and supernatant was dispensed to a new 96-well plate. With use of a plate reader, the intensity of light emission at Ex/Em=$355/460$ nm was measured, and, thus, antigen was detected.
⑤ Apart from the above, the treatment of ② to ⑤ was conducted without the treatment of ①, and, thus, the amount of non-specific adsorption was found.

TABLE 3

Conditions for the preparation of antigen-coated dynabeads, and evaluation

| Name of blocking agents | Number | Beads (μg) | Antigen (μg) | blocking agents (μL) | Antibody (ALP conj.) (μL) | 4-MUP (μL) | 0.5M NaOH aq (μL) |
|---|---|---|---|---|---|---|---|
| PEHA-PEG (P/B = 10) | A-9 | 31.25 | 10 | 50 | | | |
| | C-9 | 31.25 | — | | | | |
| BSA | A-10 | 31.25 | 10 | | 50 | 100 | 35 |
| | C-10 | 31.25 | — | | | | |
| no block | A-11 | 31.25 | 10 | — | | | |
| | C-11 | 31.25 | — | | | | | antigen solution: Antigen (Goat-IgG) was dissolved in TB.
0.65 wt % blocking agent solution: Blocking agents (PEHA-Phenyl-PEG, BSA) were dissolved in TB.
antibody solution: Antibody (alkaliphosphatase conjugate
anti-goat-IgG) was diluted with TBS to the concentration of 1/30,000.
Substrate: 4-Methylumbelliferyl phosphate (4-MUP)

Figure 11:
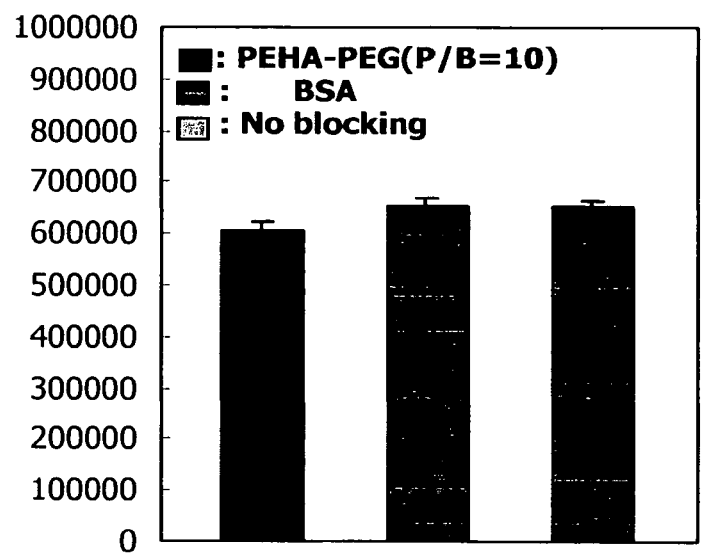
FIG. 11 is a graph which shows the result of surface treatment of dynabeads antibody-supporting magnetic particles with PEHA-Ph-PEG-OH. It is seen that antigen-detecting ability was high enough.
Figure 12:
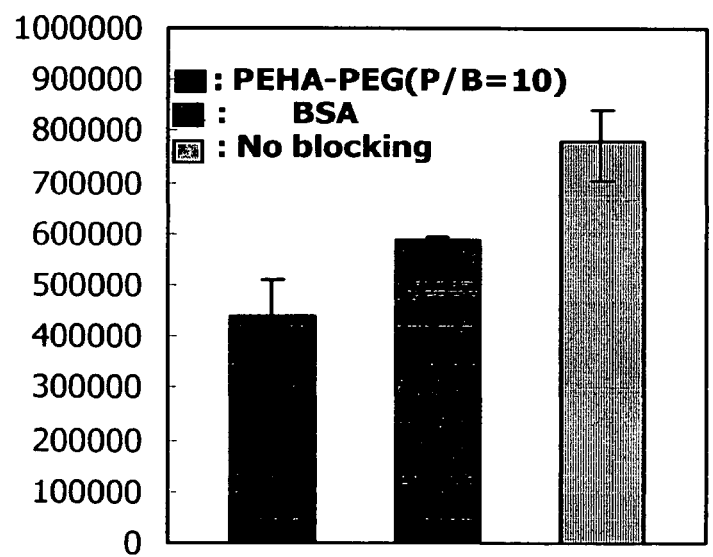
FIG. 12 is a graph which shows the result of surface treatment of dynabeads antibody-supporting magnetic particles with PEHA-Ph-PEG-OH. It is seen that non-specific adsorption is inhibited by surface treatment.

The amount of antibody detected is shown in FIG. 11, and the amount of non-specific adsorption is shown in FIG. 12. It was confirmed that, even when blocking was conducted with PEHA-Phenyl-PEG-OH, detection sensitivity did not decrease, and that non-specific adsorption was remarkably restrained.

Figure 13:
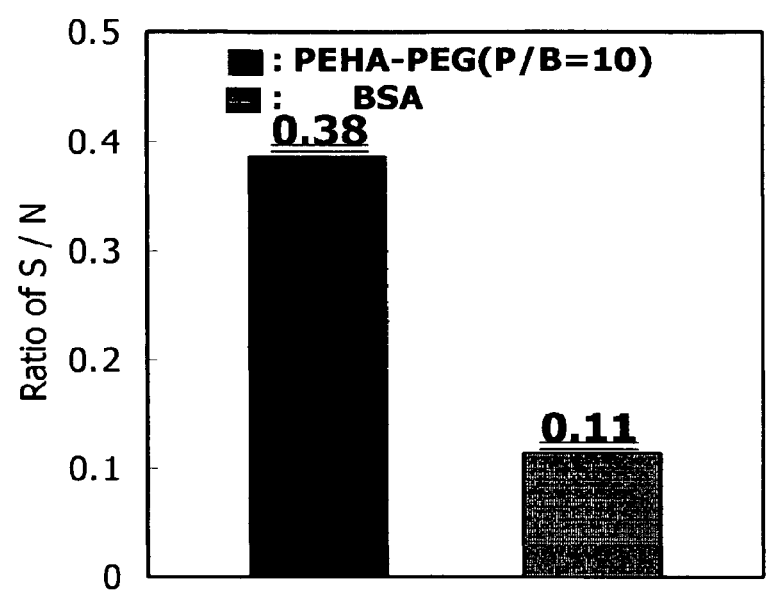
FIG. 13 shows both the result of surface treatment of dynabeads antibody-supporting magnetic particles with PEHA-Ph-PEG-OH and S/N.

FIG. 13 shows S/N ratio. It is more effective than albumin blocking.

Example 14: Western Blot Technique (1)

Figure 14:
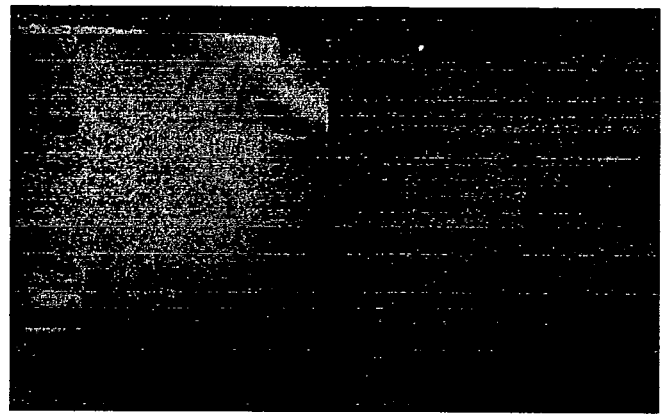
FIG. 14 are photographs in place of drawings which show whether or not fluorescence-labeled protein was non-specifically adsorbed onto PVDF membrane for western blotting.
Figure 14:
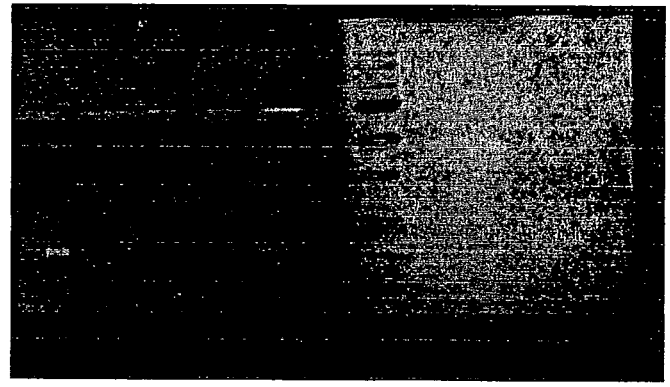

With use of western blot technique as a BSA-detecting system, a comparison was made between blocking agents and the polymer of the present invention. BSA which had been separated by SDS polyacrylamide gel electrophoresis (SDS-PAGE) was transferred from gel to polyvinylidene fluoride (PVDF) membrane (Immobilon-P manufactured by Nippon Millipore Co.) at a constant currency of 1 mA per 1 cm$^2$ for two hours. Comparison on performance as a blocking agent was made among gelatin (EIA grade reagent manufactured by Bio-Rad Co.), acetal-polyethyleneglycol/poly-methacrylic acid dimethylaminoethyl block polymer (acetal-PEG-b-PAMA) and methoxy-polyethyleneglycol/polylactic acid block polymer (two species of different molecular weight, i.e., methoxy-PEG-PLA5000 and methoxy-PEG-PLA500, were used). Blocking operation was conducted as follows: A membrane to which BSA had been transferred was dipped in a 1% polymer-containing PBS solution, and was mildly shaken either for two hours at room temperature or overnight at 4° C. Detection was conducted by fluorescence-labeled streptoavidin and with use of anti-BSA antibody (rabbit) as a primary antibody, and of biotin-labeled anti-rabbit antibody (donkey). Results are shown in FIG. 14, from which it is seen that the polymer of the present invention achieved excellent non-specific adsorption-restraining effect as compared with conventionally used gelatin.

Example 15: Coating Treatment of Glass Surface with PEG

PEG graft chain was constructed on glass substrate surface with use of a surface treating agent of the present invention. For measurement, there were used two species of acetal-PEG-b-PAMA (sample ①: PEG Mw=4,600, PAMA Mw=3,800; ②; PEG Mw=10,000, PAMA Mw=3,800). Glass plate (15×30×1 mm) to be used for ζ potential measurement was subjected, before use, to boiling-washing for one hour at 80° C. with use of a piranha solution of concentrated sulfuric acid:hydrogen peroxide water=1:1. After the piranha solution was replaced with deionized water several times, the glass plate was subjected to ultrasonic cleaning for 10 minutes.

Coating treatment ①: (adsorption in hot water bath and under acidic conditions; activation of molecular motion) In harmony with ionic intensity at the time of potential measurement, and for the purpose of accelerating protonation of PAMA, there was prepared 7.5 mM aqueous solution of HCl (pH=2.1) in a test tube, and, with use of 10 ml of this solution, 0.5 wt % acetal-PEG-b-PAMA solution was produced in hot water bath at 50° C. and 80° C. Glass was dipped in this acetal-PEG-b-PAMA solution for one hour with temperature maintained, and, thus, glass surface was treated.

Coating treatment ②: (adsorption in a high salt concentration of aqueous solution and under acidic conditions at room temperature) There was prepared 10 ml of 7.5 mM aqueous solution of HCl (pH=2.1) which contained 1 M NaCl, and, in the aqueous solution, acetal-PEG-b-PAMA was dissolved at a concentration of 1 mg/ml. To the resultant solution, glass was dipped and left to stand still for 30 minutes at room temperature. Then, the glass was washed with 1 M NaCl-containing 7.5 mM aqueous solution of HCl (pH=2.1), and was subsequently left to stand still for 30 minutes in the above-mentioned PEG aqueous solution, and, thus, glass surface was treated.

Thus prepared samples were used for the evaluation of electroosmotic flow-restraining effect of surface treatment, on the basis of pH dependency of ζ potential.

Figure 15:
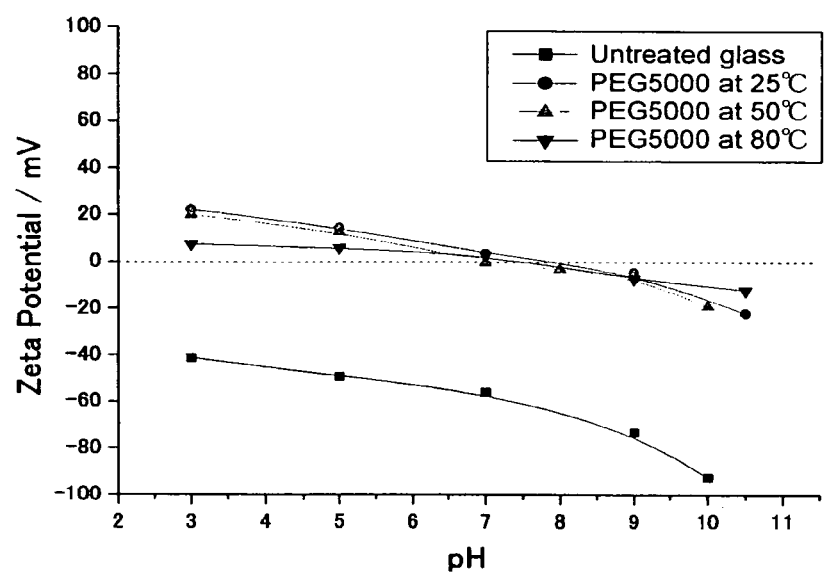
FIG. 15 is a graph which shows the comparison of surface potential of glass surface treated with acetal-PEG-b-PAMA.

Measurement of ζ potential: Measurement was conducted by laser Doppler method with use of LEZA-600 apparatus of Otsuka Electronics Co., Ltd. For the measurement of pH dependency of ζ potential, pH value was raised from acidic side, i.e., pH 3, 5, 7, 8, 9 up to 10. Measurement was made two or three times at each pH, and a stable value was employed as a measurement value.

pH Dependency of ζ potential: FIG. 15 shows a comparison of pH dependency of ζ potential between the surface of unmodified glass and the surface of PEG-modified glass which had undergone adsorption treatment at 25, 50 and 80° C. The use of acetal-PEG-b-PAMA gave a surface on which surface potential change caused by pH was small, and which was hardly susceptible to outer environment, as compared with unmodified glass.

Example 16: Western Blot Technique (2)

With use of alkaliphosphatase-labeled secondary antibody as a color-developing system in western blot technique, a comparison was made between the block copolymer of the present invention and conventionally used blocking agents with regard to blocking effect in a system to detect α-feto protein (hereinafter referred to as AFP). As samples, there were prepared ① AFP diluted to 8,000 IU/ml with normal human serum which had been diluted to ¹⁄₁₀ strength; and ② AFP diluted to 8,000 IU/ml with a cell extract having a protein concentration of 20 μg/ml. With use of these samples and in accordance with the method as mentioned in Example 14, comparison on blocking effect was made between bovine serum albumin (BSA) and methoxy-polyethyleneglycol/polylactic acid block polymer (PEG-PLA).

For detection, there were used anti-AFP antibody (rabbit) as a primary antibody, alkaliphosphatase-labeled anti-rabbit antibody (donkey) as a secondary antibody, and 5-bromo-4-chloro-3-indolylphosphate/nitroblue tetrazolium (BCIP/NBPT) as a substrate.

Figure 16:
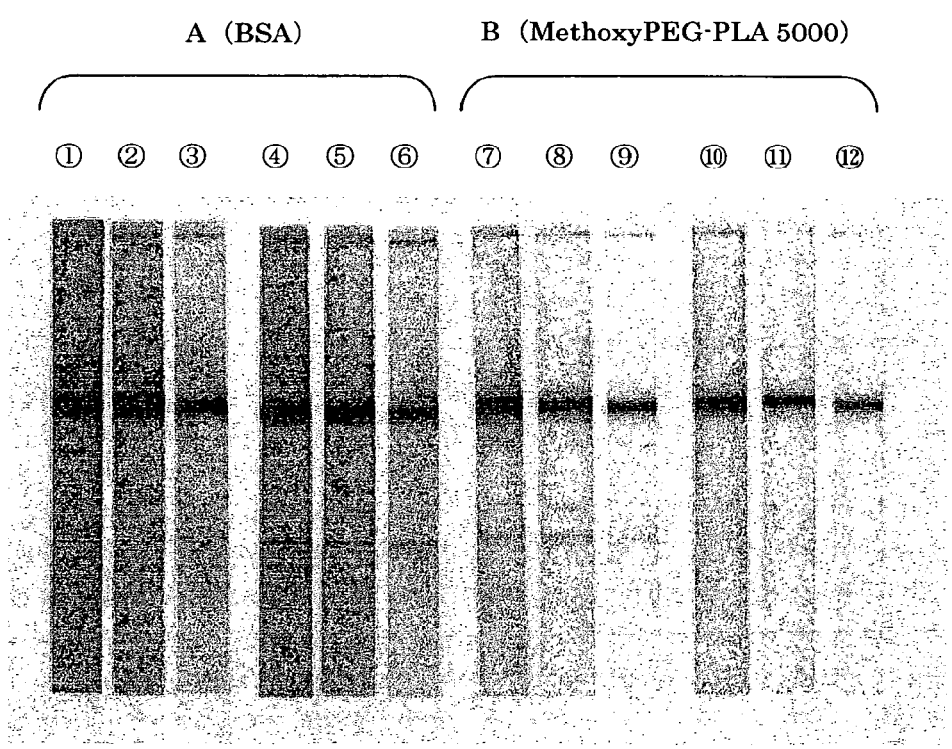
FIG. 16 is a photograph in place of drawing which shows the result of western blotting conducted in accordance with Example 16.

Results are shown in FIG. 16, from which it is seen that the surface treating agent MethoxyPEG-PLA5000 of the present invention achieved the reduction of background owing to its excellent non-specific adsorption-restraining effect, as compared with conventionally used BSA.

Abbreviation and numbers in FIG. 16 have the following meanings:
A: BSA was used.
① Primary antibody diluted to ¹⁄₅₀₀₀ strength, Secondary antibody diluted to ¹⁄₂₅₀₀ strength;
② Primary antibody diluted to ¹⁄₅₀₀₀ strength, Secondary antibody diluted to ¹⁄₅₀₀₀ strength;
③ Primary antibody diluted to ¹⁄₅₀₀₀ strength, Secondary antibody diluted to ¹⁄₁₀₀₀₀ strength;
④ Primary antibody diluted to ¹⁄₁₀₀₀₀ strength, Secondary antibody diluted to ¹⁄₂₅₀₀ strength;
⑤ Primary antibody diluted to ¹⁄₁₀₀₀₀ strength, Secondary antibody diluted to ¹⁄₅₀₀₀ strength;
⑥ Primary antibody diluted to ¹⁄₁₀₀₀₀ strength, Secondary antibody diluted to ¹⁄₁₀₀₀₀ strength.

B: MethoxyPEG-PLA5000 was used.
⑦ Primary antibody diluted to ¹⁄₅₀₀₀ strength, Secondary antibody diluted to ¹⁄₂₅₀₀ strength;
⑧ Primary antibody diluted to ¹⁄₅₀₀₀ strength, Secondary antibody diluted to ¹⁄₅₀₀₀ strength;
⑨ Primary antibody diluted to ¹⁄₅₀₀₀ strength, Secondary antibody diluted to ¹⁄₁₀₀₀₀ strength;
⑩ Primary antibody diluted to ¹⁄₁₀₀₀₀ strength, Secondary antibody diluted to ¹⁄₂₅₀₀ strength;
⑪ Primary antibody diluted to ¹⁄₁₀₀₀₀ strength, Secondary antibody diluted to ¹⁄₅₀₀₀ strength;
⑫ Primary antibody diluted to ¹⁄₁₀₀₀₀ strength, Secondary antibody diluted to ¹⁄₁₀₀₀₀ strength.

Example 17: Surface Treatment of Microcircuit with PEG Segment-Containing Graft Copolymer Consideration was given to the modification of silicone compound surface with PEG graft polymer, and to protein adsorption.

Preparation of silicone compound: With use of SILIGARD 184 ELASTMER KIT manufactured by Dow Corning Co., a mixture of SILICONE ELASTMER:SILICONE ELASTMER CURING AGENT=10:1 (by weight) was prepared, poured into glass-made mold, and was treated for one hour at 65° C., and further for one hour at 100° C., to give a silicone base.

Silicone surface which had been prepared in the above-mentioned method was washed, and was then made to react with polymethoxysilylpropyl methacrylate-PEG graft copolymer (PTSPM-g-PEG$_{1100}$) and PEG homopolymer (PEG$_{1100}$) each for four hours at room temperature, and, thus, silicone surface was modified with PEG brush.

Figure 17:
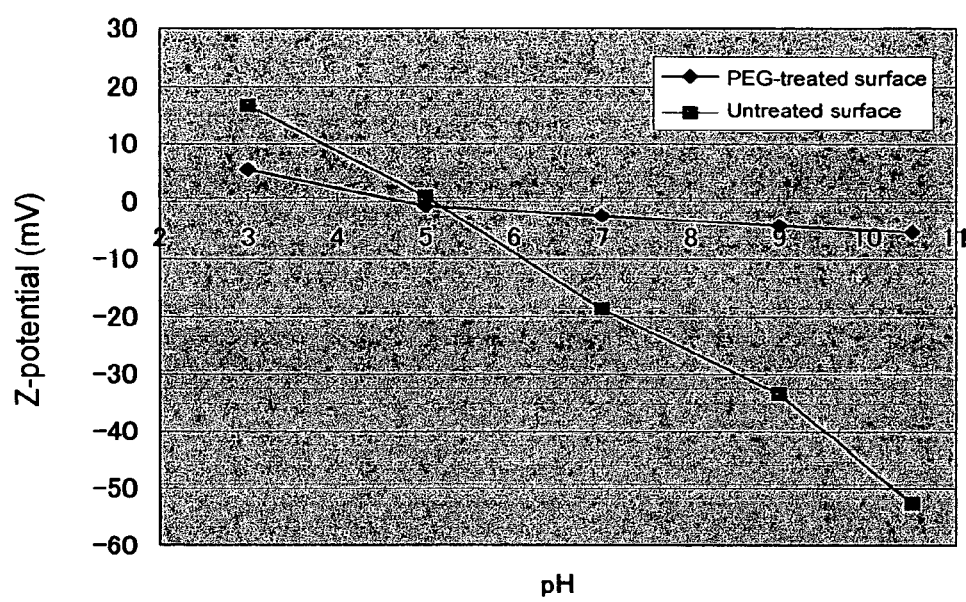
FIG. 17 shows a comparison of surface potential between silicone surface which was treated with polytrimethoxysilylpropyl methacrylate-PEG graft copolymer (PTSPM-g-$PEG_{1100}$) and untreated silicone surface.

Comparison on ζ potential was made between surfaces which had been prepared in the above-mentioned manner. Result is shown in FIG. 17. As is seen in FIG. 17, the surface which had been treated by the method of the present invention showed only a small change of ζ potential caused by pH, was electrically neutral and had weak ionic interaction.

Example 18: Collective Surface Treating Method Wherein, when Polydimethoxy Silyl (PPMS) is Formed, Either PTSPM-g-PEG or PEG Macromonomer Having Polymerizable Vinyl Group is Applied on Mold Surface When PDMS which was to be a base was polymerized, glass surface was directly spin-coated with PEG-containing graft copolymer, i.e., PTSPM-g-PEG$_{1100}$. Thus coated glass was used as a mold, by which PDMS was polymerized and simultaneously surface-treated with PEG. Then evaluation by potential was conducted.

Figure 18:
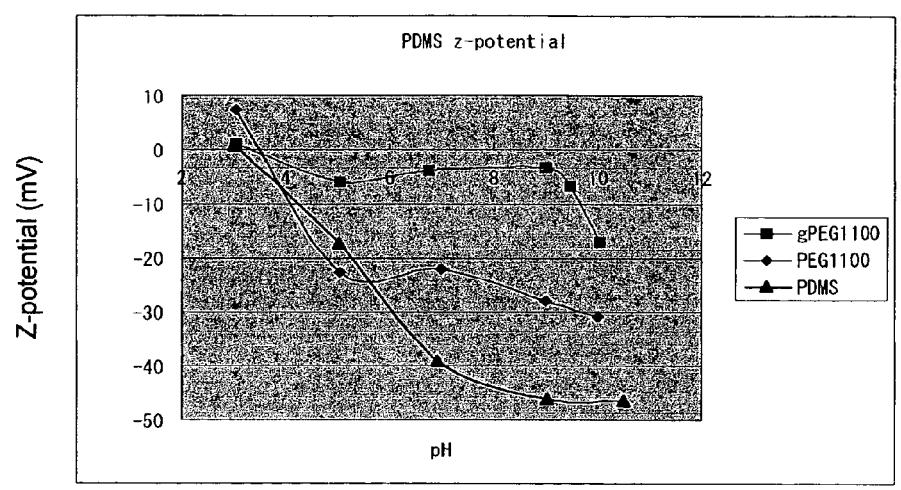
FIG. 18 shows the result of a comparison of surface potential of silicone which was formed from a mold of glass whose cleansed surface had been coated with polytrimethoxysilylpropyl methacrylate-PEG graft copolymer (PTSPM-g-$PEG_{1100}$) and which was thereby simultaneously treated, with surface potential of untreated silicone surface and with surface potential of a surface treated with polyethylene glycol homopolymer.

The surface which had been treated in the above-mentioned manner was evaluated with respect to potential and non-specific adsorption of bovine serum. Results are shown in FIG. 18. Untreated silicone surface was negatively charged, whereas silicone surface treated with PTSPM-g-PEG$_{1100}$ was almost neutral in a range of pH 4 to 8, which means that the surface had been modified with PEG brush.

Figure 19:
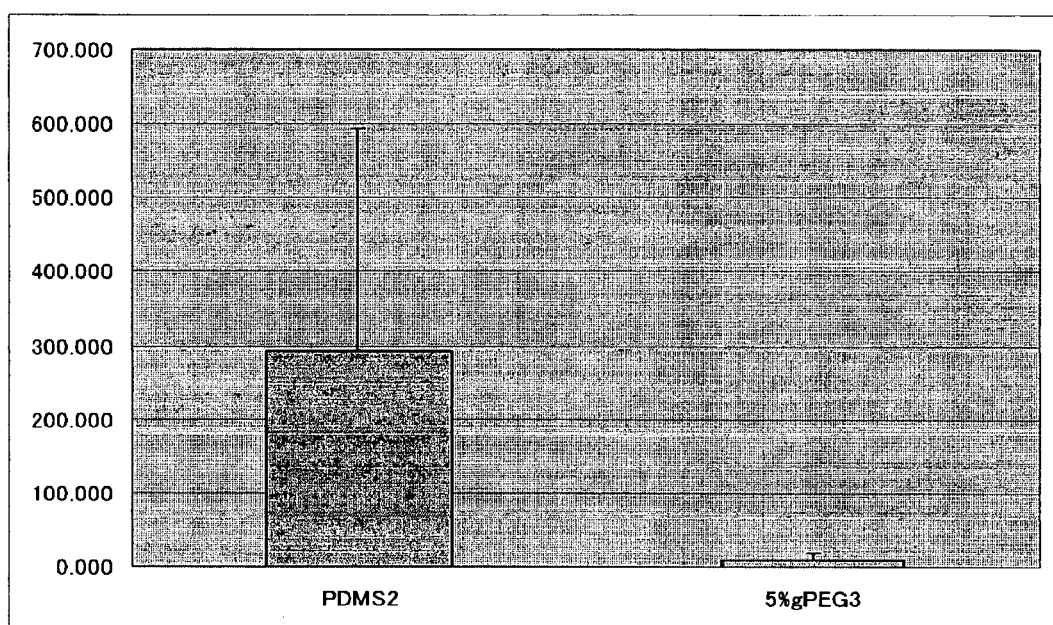
FIG. 19 is a graph which shows the result of a comparison of adsorptivity of fluorescence-labeled human IgG onto a surface-treated silicone surface, with untreated surface.
Figure 20:
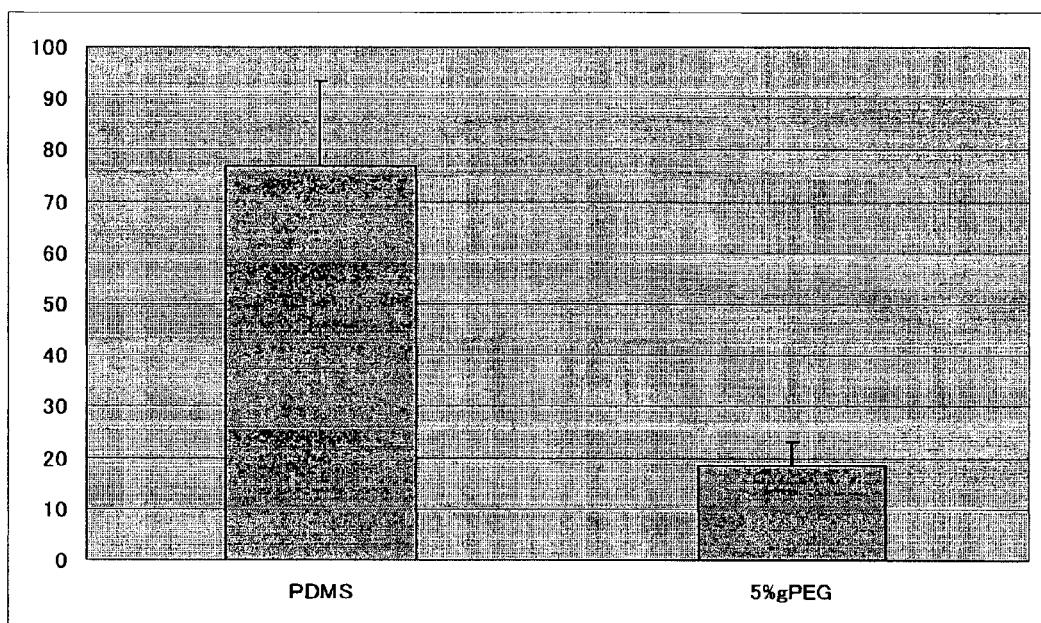
FIG. 20 is a graph which shows the result of a comparison of adsorptivity of fluorescence-labeled bovine serum albumin onto a surface-treated silicone surface, with untreated surface.

Non-specific adsorption of protein to treated surface was evaluated with use of fluorescence-labeled albumin and IgG. Results are shown by FIG. 19 and FIG. 20. Surface treatment achieved remarkable reduction of adsorptivity of both proteins. Furthermore, whereas the untreated silicone surface showed a large scattering in the amount of adsorption, the treated surface restrained non-specific adsorption with good reproducibility.

INDUSTRIAL APPLICABILITY

This invention provides a surface of substrate of biosensor to which the non-specific adsorption of impurity proteins such as blood and plasma which exist in sample is significantly restrained. This invention is therefore usable in biosensor-manufacturing industries or in the field of clinical diagnosis which uses biosensor.

The invention claimed is:
1. A substrate surface comprising:
   (i) either a substance to detect analyte or an analyte per se immobilized on the substrate surface, and
   (ii) an uncrosslinked polymer based on a polyethylene glycol chain segment formed by treating the substrate surface with a liquid comprising the uncrosslinked polymer based on the polyethylene glycol chain segment, wherein the treatment is conducted after the substance or analyte is immobilized on the substrate surface,
   wherein the substrate surface is selected from the group consisting of an electrochemical sensor surface, a surface plasmon sensor surface, a quartz sensor surface, a microplate surface for a solid phase enzyme-linked immunoassay (ELISA), a plastic film surface for protein blotting or nucleic acid blotting, a microarray surface for the hybridization of nucleic acid, a gold particle surface, a semiconductor nano particle surface, a silica particle surface, a fine porous particle surface and a particle surface of latex which contains one of the above-mentioned particles, and
   wherein the uncrosslinked polymer based on the polyethylene glycol chain segment has formula (I) as follows:

$$R^1\text{-}L_1\text{-}(CH_2CH_2O)_n\text{-}L_2\text{-}X \quad (I)$$

wherein $R^1$ denotes a hydrogen atom, methyl, formyl which is protected, amino which is protected, carboxy which is protected, or hydroxyl which is protected;
   $L_1$ is a linker selected from the group consisting of
   $-(CH_2)_p-O-$, $-(CH_2)_q-COO-$,

and $-(CH_2)_r-S-$,
   wherein p, q and r independently denote an integer of 0 to 8;
   $L_2$ is a linker selected from the group consisting of
   $-(CH_2)_k-$, $-CO(CH_2)_l-$ and

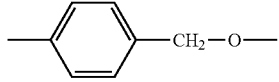

wherein k denotes an integer of 0-6 and l denotes an integer of 1 to 6;
   X is bonded to the substrate surface, and
   X is selected from the group consisting of:
   (i) a chain of the formula:

$-(CH_2CH_2NH)_m-R^2,$ wherein $R^2$ denotes a hydrogen atom or a lower alkyl group, and m denotes an integer of 1 to 2,000;
   (ii) a chain of the formula:

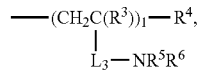

wherein
   $R^3$, $R^4$, $R^5$ and $R^6$ each independently denote a hydrogen atom or a lower alkyl group,
   l denotes an integer of 1 to 2,000,
   $L_3$ is selected from the group consisting of:

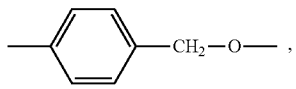

$-CONH(CH_2)_p-$ and $-CONR^7(CH_2)_p-$,
   wherein p denotes an integer of 1 to 10, and $R^7$ denotes a lower alkyl which may have a hetero atom;
   (iii) a chain of the formula:

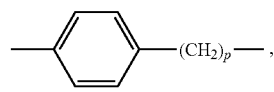

wherein $R^3$, $R^4$, l and $L_3$ are as defined above, and $R^8$ denotes a lower alkyl or a halogen atom; and
   (iv) a chain of the formula:

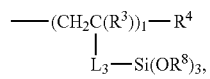

wherein $R^3$, $R^4$ and l are as defined above; and
   n denotes an integer of 2 to 20,000.
2. The substrate surface of claim 1, wherein the substance to detect analyte or analyte per se is one companion piece to a specific bonding pair.
3. The substrate surface of claim 2, wherein the one companion piece to a specific bonding pair is selected from the group consisting of an antigen, a hapten, an antibody, an oligonucleotide, an enzyme, a substrate of enzyme, a sugar, lectin, a hormone, a receptor protein, avidin and biotin.
4. A method to produce the substrate surface of claim 1, which comprises:
   (A) contacting a substrate surface with an aqueous solution comprising a substance to detect analyte or an analyte per se such that the substance or the analyte is immobilized on the substrate surface, then
   (B) treating substrate having the immobilized substance or analyte with a liquid comprising an uncrosslinked polymer based on a polyethylene glycol chain segment,
   wherein the substrate surface is selected from the group consisting of an electrochemical sensor surface, a surface plasmon sensor surface, a quartz sensor surface, a microplate surface for a solid phase enzyme-linked immunoassay (ELISA), a plastic film surface for protein blotting or nucleic acid blotting, a microarray surface for the hybridization of nucleic acid, a gold particle surface, a semiconductor nano particle surface, a silica particle surface, a fine porous particle surface and a particle surface of latex which contains one of the above-mentioned particles, and wherein the uncrosslinked polymer based on the polyethylene glycol chain segment has formula (I) as follows:

 (I)

wherein $R^1$ denotes a hydrogen atom, methyl, formyl which is protected, amino which is protected, carboxy which is protected, or hydroxyl which is protected;

$L_1$ is a linker selected from the group consisting of $-(CH_2)_p-O-$, $-(CH_2)_q-COO-$,

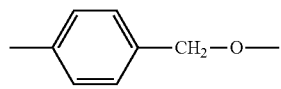

and $-(CH_2)_r-S-$, wherein p, q and r independently denote an integer of 0 to 8;

$L_2$ is a linker selected from the group consisting of $-(CH_2)_k-$, $-CO(CH_2)_l-$ and

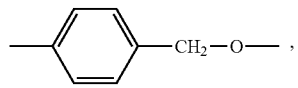

wherein k denotes an integer of 0 to 6 and l denotes an integer of 1-6;

wherein said treating immobilized the uncrosslinked polymer to the substrate surface and wherein.

X wherein said treating immobilized the uncrosslinked polymer to the substrate surface and wherein is bonded to the substrate surface, and X is selected from the group consisting of:

(i) a chain of the formula:

wherein $R^2$ denotes a hydrogen atom or a lower alkyl group, and m denotes an integer of 1 to 2,000;

(ii) a chain of the formula:

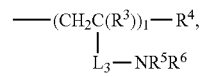

wherein $R^3$, $R^4$, $R^5$ and $R^6$ each independently denote a hydrogen atom or a lower alkyl group, l denotes an integer of 1 to 2,000, $L_3$ is selected from the group consisting of:

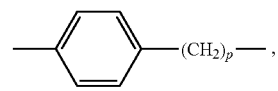

$-CONH(CH_2)_p-$ and $-CONR^7(CH_2)_p-$;

wherein p denotes an integer of 1 to 10, and $R^7$ denotes a lower alkyl which may have a hetero atom;

(iii) a chain of the formula:

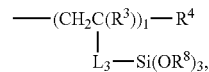

wherein $R^3$, $R^4$, l and $L_3$ are as defined above, and $R^8$ denotes a lower alkyl or a halogen atom; and (iv) a chain of the formula:

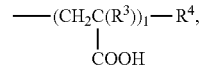

wherein $R^3$, $R^4$ and l are as defined above; and n denotes an integer of 2 to 20,000.

5. A biosensor which is equipped with the substrate surface of claim 1.

6. A biosensor which is equipped with the substrate surface of claim 2.

7. A biosensor which is equipped with the substrate surface of claim 3.

* * * * *